(12) United States Patent
de la Rama et al.

(10) Patent No.: US 8,974,454 B2
(45) Date of Patent: Mar. 10, 2015

(54) KIT FOR NON-INVASIVE ELECTROPHYSIOLOGY PROCEDURES AND METHOD OF ITS USE

(75) Inventors: Alan de la Rama, Cerritos, CA (US); Cary Hata, Irvine, CA (US); William Du, Walnut, CA (US); Yongxing Zhang, Irvine, CA (US); James V. Kauphusman, Newport Beach, CA (US); Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 835 days.

(21) Appl. No.: 12/982,715

(22) Filed: Dec. 30, 2010

(65) Prior Publication Data
US 2011/0288392 A1 Nov. 24, 2011

Related U.S. Application Data

(63) Continuation-in-part of application No. 12/651,074, filed on Dec. 31, 2009.

(60) Provisional application No. 61/355,242, filed on Jun. 16, 2010.

(51) Int. Cl.
*A61B 18/14* (2006.01)
*A61M 25/00* (2006.01)
(Continued)

(52) U.S. Cl.
CPC ....... *A61M 25/0068* (2013.01); *A61M 25/0013* (2013.01); *A61M 25/0054* (2013.01); *A61M 25/0069* (2013.01); *A61M 25/0074* (2013.01);
(Continued)

(58) Field of Classification Search
USPC ........ 606/41, 45–50; 607/101, 102, 115, 116, 607/122
See application file for complete search history.

(56) References Cited

U.S. PATENT DOCUMENTS 4,325,374 A 4/1982 Komiya
5,163,905 A 11/1992 Don Michael
(Continued)

FOREIGN PATENT DOCUMENTS

CN 1897885 1/2007
EP 0109178 A2 5/1984
(Continued)

OTHER PUBLICATIONS

International Search Report and Written Opinion of the International Searching Authority, PCT/US2010/049836 Nov. 15, 2010.
(Continued)

*Primary Examiner* — Michael Peffley
(74) *Attorney, Agent, or Firm* — Wiley Rein LLP

(57) ABSTRACT

An electrophysiology catheter for use with a steerable introducer sheath includes a flexible catheter body having a proximal end and a distal end and at least one hollow elongate tip electrode disposed at the distal end of the catheter body. The hollow elongate tip electrode includes a sidewall having at least one elongate gap that provides flexibility allowing the tip electrode to bend relative to a longitudinal axis of the catheter body. The catheter body is an independent, non-steerable structure, and can be moved via movement of the steerable introducer through which it is introduced into a patient.

20 Claims, 20 Drawing Sheets

(51) Int. Cl.
    *B23K 26/38* (2014.01)
    *B23K 26/40* (2014.01)
    *A61B 5/04* (2006.01)
    *A61B 18/00* (2006.01)
    *A61B 19/00* (2006.01)
    *A61M 25/01* (2006.01)
    *A61M 25/06* (2006.01)
    *B26D 1/00* (2006.01)
    *B26D 3/08* (2006.01)

(52) U.S. Cl.
    CPC ......... *A61M 25/008* (2013.01); *A61M 25/0082* (2013.01); *B23K 26/38* (2013.01); *B23K 26/40* (2013.01); *A61B 5/04* (2013.01); *A61B 18/1492* (2013.01); *A61B 2018/00011* (2013.01); *A61B 2018/00101* (2013.01); *A61B 2018/00577* (2013.01); *A61B 2018/00821* (2013.01); *A61B 2018/00839* (2013.01); *A61B 2019/465* (2013.01); *A61B 2217/007* (2013.01); *A61B 2218/002* (2013.01); *A61M 25/0133* (2013.01); *A61M 2025/0081* (2013.01); *A61M 2025/0681* (2013.01); *B23K 2201/36* (2013.01); *B26D 1/00* (2013.01); *B26D 3/08* (2013.01)
    USPC ............................................ 606/41; 607/122

(56) References Cited

U.S. PATENT DOCUMENTS

| | | | |
|---|---|---|---|
| 5,279,299 A | 1/1994 | Imran | |
| 5,378,230 A | 1/1995 | Mahurkar | |
| 5,462,521 A | 10/1995 | Brucker et al. | |
| 5,487,385 A | 1/1996 | Avitall | |
| 5,520,682 A | 5/1996 | Baust et al. | |
| 5,545,200 A | 8/1996 | West et al. | |
| 5,681,280 A | 10/1997 | Rusk et al. | |
| 5,772,642 A | 6/1998 | Ciamacco, Jr. et al. | |
| 5,800,428 A | 9/1998 | Nelson et al. | |
| 5,833,632 A | 11/1998 | Jacobsen et al. | |
| 5,893,885 A | 4/1999 | Webster, Jr. | |
| 5,902,328 A | 5/1999 | LaFontaine et al. | |
| 5,919,188 A | 7/1999 | Shearon et al. | |
| 5,944,022 A * | 8/1999 | Nardella et al. | 128/899 |
| 5,951,471 A | 9/1999 | De la Rama et al. | |
| 5,954,719 A | 9/1999 | Chen et al. | |
| 5,992,418 A | 11/1999 | de la Rama et al. | |
| 6,001,095 A | 12/1999 | de la Rama et al. | |
| 6,010,500 A | 1/2000 | Sherman et al. | |
| 6,017,338 A | 1/2000 | Brucker et al. | |
| 6,030,382 A * | 2/2000 | Fleischman et al. | 606/41 |
| 6,053,912 A | 4/2000 | Panescu et al. | |
| 6,063,080 A * | 5/2000 | Nelson et al. | 606/41 |
| 6,200,315 B1 * | 3/2001 | Gaiser et al. | 606/41 |
| 6,210,409 B1 | 4/2001 | Ellman et al. | |
| 6,217,573 B1 | 4/2001 | Webster | |
| 6,233,476 B1 | 5/2001 | Strommer et al. | |
| 6,235,022 B1 | 5/2001 | Hallock et al. | |
| 6,251,134 B1 | 6/2001 | Alt | |
| 6,273,876 B1 | 8/2001 | Klima et al. | |
| 6,308,090 B1 | 10/2001 | Tu et al. | |
| 6,325,797 B1 | 12/2001 | Stewart et al. | |
| 6,346,104 B2 | 2/2002 | Daly et al. | |
| 6,356,790 B1 | 3/2002 | Maguire et al. | |
| 6,385,472 B1 | 5/2002 | Hall et al. | |
| 6,405,067 B1 | 6/2002 | Mest et al. | |
| 6,464,632 B1 | 10/2002 | Taylor et al. | |
| 6,493,590 B1 * | 12/2002 | Wessman et al. | 607/116 |
| 6,498,944 B1 | 12/2002 | Ben-Haim et al. | |
| 6,522,930 B1 | 2/2003 | Schaer et al. | |
| 6,604,003 B2 | 8/2003 | Fredricks et al. | |
| 6,611,699 B2 | 8/2003 | Messing | |
| 6,662,034 B2 | 12/2003 | Segner et al. | |
| 6,690,963 B2 | 2/2004 | Ben-Haim et al. | |
| 6,780,183 B2 | 8/2004 | Jimenez, Jr. et al. | |
| 6,788,967 B2 | 9/2004 | Ben-Haim et al. | |
| 6,921,397 B2 | 7/2005 | Corcoran et al. | |
| 6,980,843 B2 | 12/2005 | Eng | |
| 7,013,169 B2 | 3/2006 | Bowe | |
| 7,137,395 B2 | 11/2006 | Fried et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,389,148 B1 * | 6/2008 | Morgan | 607/116 |
| 7,416,552 B2 | 8/2008 | Paul et al. | |
| 7,468,027 B2 | 12/2008 | Barbut et al. | |
| 7,536,218 B2 | 5/2009 | Govari et al. | |
| 7,537,595 B2 | 5/2009 | McClurken | |
| 7,565,208 B2 | 7/2009 | Harris et al. | |
| 7,615,050 B2 * | 11/2009 | Cross et al. | 606/41 |
| 7,669,309 B2 | 3/2010 | Johnson et al. | |
| 7,699,771 B2 | 4/2010 | Wendlandt et al. | |
| 7,706,891 B2 | 4/2010 | Hastings et al. | |
| 7,815,635 B2 | 10/2010 | Wittkampf et al. | |
| 7,824,406 B2 | 11/2010 | Wang et al. | |
| 7,824,517 B2 | 11/2010 | Kampa et al. | |
| 7,826,881 B1 | 11/2010 | Beatty et al. | |
| 7,857,810 B2 | 12/2010 | Wang et al. | |
| 7,873,401 B2 | 1/2011 | Shachar | |
| 8,048,072 B2 | 11/2011 | Verin et al. | |
| 8,187,267 B2 | 5/2012 | Pappone et al. | |
| 2001/0012956 A1 | 8/2001 | Behl | |
| 2002/0058866 A1 | 5/2002 | Segner et al. | |
| 2002/0103426 A1 | 8/2002 | Segner et al. | |
| 2002/0156420 A1 | 10/2002 | Andersn et al. | |
| 2003/0088244 A1 | 5/2003 | Swanson et al. | |
| 2003/0125730 A1 | 7/2003 | Berube et al. | |
| 2004/0015215 A1 | 1/2004 | Fredricks et al. | |
| 2004/0034348 A1 | 2/2004 | Rashidi | |
| 2004/0153056 A1 | 8/2004 | Muller et al. | |
| 2004/0181138 A1 | 9/2004 | Hindricks et al. | |
| 2004/0204671 A1 | 10/2004 | Stubb | |
| 2004/0220461 A1 | 11/2004 | Schwartz | |
| 2004/0231683 A1 | 11/2004 | Eng et al. | |
| 2004/0236350 A1 | 11/2004 | Lewis et al. | |
| 2004/0243143 A1 | 12/2004 | Corcoran et al. | |
| 2004/0267106 A1 | 12/2004 | Segner et al. | |
| 2005/0004563 A1 | 1/2005 | Racz | |
| 2005/0049583 A1 | 3/2005 | Swanson | |
| 2005/0054989 A1 | 3/2005 | McGuckin | |
| 2005/0070894 A1 | 3/2005 | McClurken et al. | |
| 2005/0096647 A1 | 5/2005 | Steinke et al. | |
| 2005/0143729 A1 | 6/2005 | Francischelli et al. | |
| 2005/0197633 A1 | 9/2005 | Schwartz | |
| 2005/0272975 A1 | 12/2005 | McWeeney | |
| 2006/0004353 A1 | 1/2006 | Koyfman et al. | |
| 2006/0064123 A1 | 3/2006 | Bonnette et al. | |
| 2006/0149192 A1 | 7/2006 | Deniega et al. | |
| 2006/0200191 A1 | 9/2006 | Zadno-Azizi | |
| 2006/0278246 A1 | 12/2006 | Eng et al. | |
| 2006/0287650 A1 | 12/2006 | Cao et al. | |
| 2007/0021743 A1 | 1/2007 | Rioux et al. | |
| 2007/0060847 A1 | 3/2007 | Leo et al. | |
| 2007/0073288 A1 | 3/2007 | Hall et al. | |
| 2007/0156114 A1 | 7/2007 | Worley et al. | |
| 2007/0179491 A1 | 8/2007 | Kratoska et al. | |
| 2007/0270791 A1 | 11/2007 | Wang et al. | |
| 2007/0299424 A1 | 12/2007 | Cumming et al. | |
| 2008/0091193 A1 | 4/2008 | Kauphusman et al. | |
| 2008/0139999 A1 | 6/2008 | Gibson et al. | |
| 2008/0161789 A1 | 7/2008 | Thao et al. | |
| 2008/0249522 A1 | 10/2008 | Pappone et al. | |
| 2008/0275428 A1 | 11/2008 | Tegg et al. | |
| 2008/0281319 A1 | 11/2008 | Paul et al. | |
| 2008/0294158 A1 * | 11/2008 | Pappone et al. | 606/41 |
| 2008/0300589 A1 | 12/2008 | Paul et al. | |
| 2008/0312713 A1 | 12/2008 | Wilfley et al. | |
| 2009/0012517 A1 | 1/2009 | de la Rama et al. | |
| 2009/0018497 A1 | 1/2009 | Birchard et al. | |
| 2009/0228092 A1 | 9/2009 | Raeder-Devens et al. | |
| 2009/0247993 A1 | 10/2009 | Kirschenman et al. | |
| 2009/0287210 A1 | 11/2009 | Kauphusman et al. | |
| 2010/0004632 A1 | 1/2010 | Wu et al. | |
| 2010/0152731 A1 | 6/2010 | De La Rama et al. | |

(56) References Cited

U.S. PATENT DOCUMENTS

| | | |
|---|---|---|
| 2010/0168560 A1* | 7/2010 | Hauck et al. ............ 600/424 |
| 2010/0174177 A1 | 7/2010 | Wu |
| 2011/0118582 A1 | 5/2011 | De La Rama et al. |
| 2012/0265130 A1 | 10/2012 | De La Rama et al. |

FOREIGN PATENT DOCUMENTS

| | | |
|---|---|---|
| JP | 2002513652 A | 5/2002 |
| JP | 2007/509693 | 4/2007 |
| WO | WO-96/34652 | 11/1996 |
| WO | 03/049631 | 6/2003 |
| WO | 03049631 | 6/2003 |
| WO | 2005/048858 | 6/2005 |
| WO | WO-2005/048858 | 6/2005 |
| WO | WO-2005/094661 | 10/2005 |
| WO | 2007/015139 | 2/2007 |
| WO | 2008/010039 | 1/2008 |
| WO | 2008124619 A1 | 10/2008 |
| WO | 2009120982 A2 | 10/2009 |
| WO | 2011159861 A2 | 12/2011 |

OTHER PUBLICATIONS

Chinese Office Action (English translation) mailed Apr. 3, 2014 in Chinese Patent Application 201080038703.3.

H. Krum et al., "Catheter-based renal sympathetic denervation for resistant hypertension: a multicentre safety and proof-of-principle cohort study", www.lhelancel.com, Mar. 30, 2009, pp. 1-7.

EP Communication for Application No. 08 745 928.5 dated Dec. 11, 2014.

\* cited by examiner

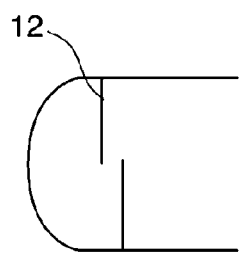
FIG. 2A
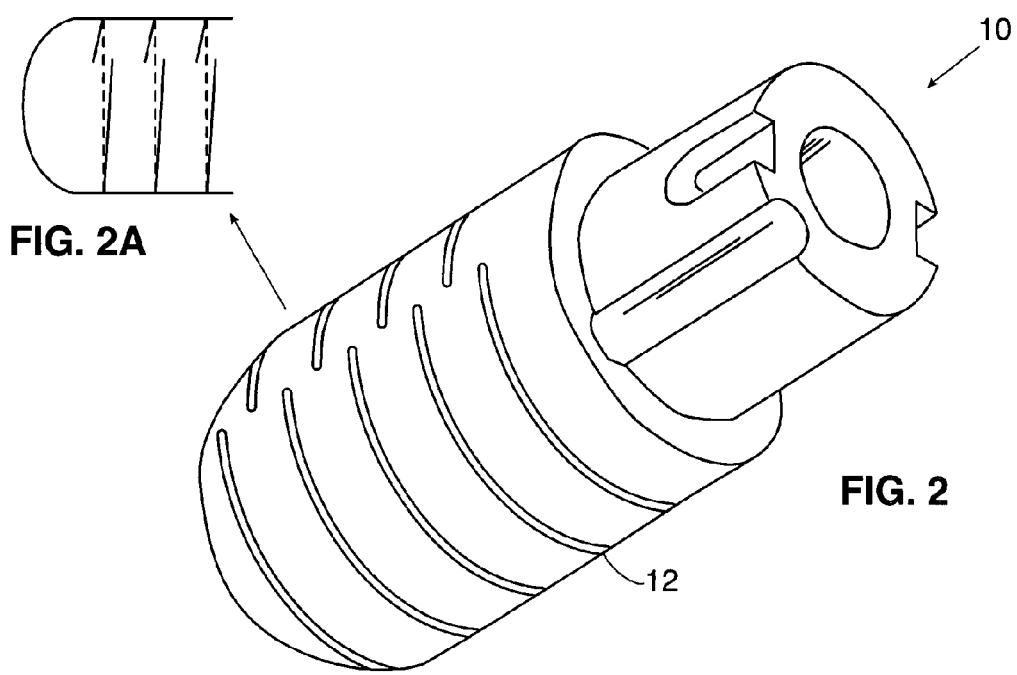
FIG. 2
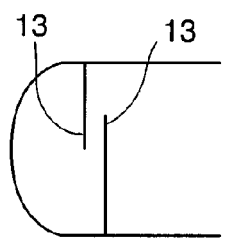
FIG. 2B
FIG. 2C
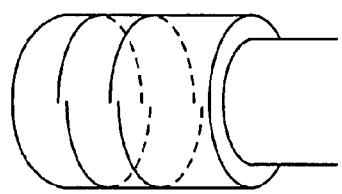
FIG. 2D

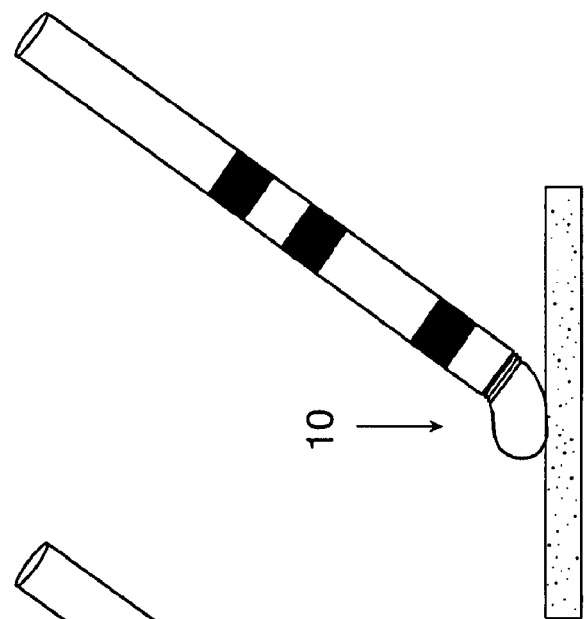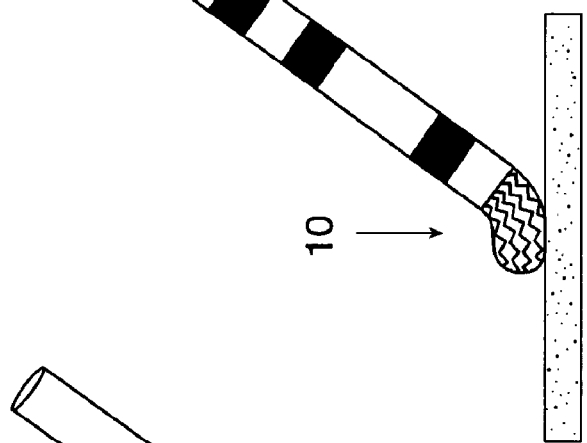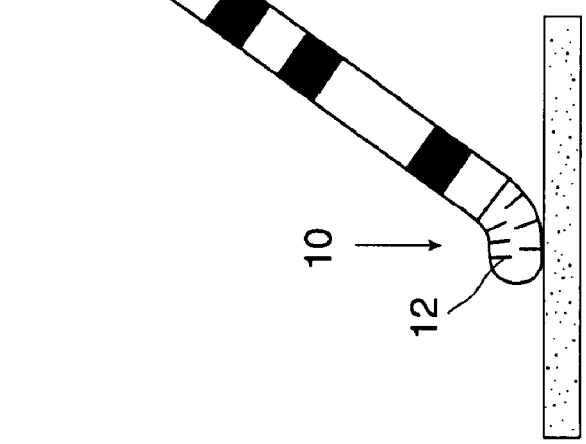

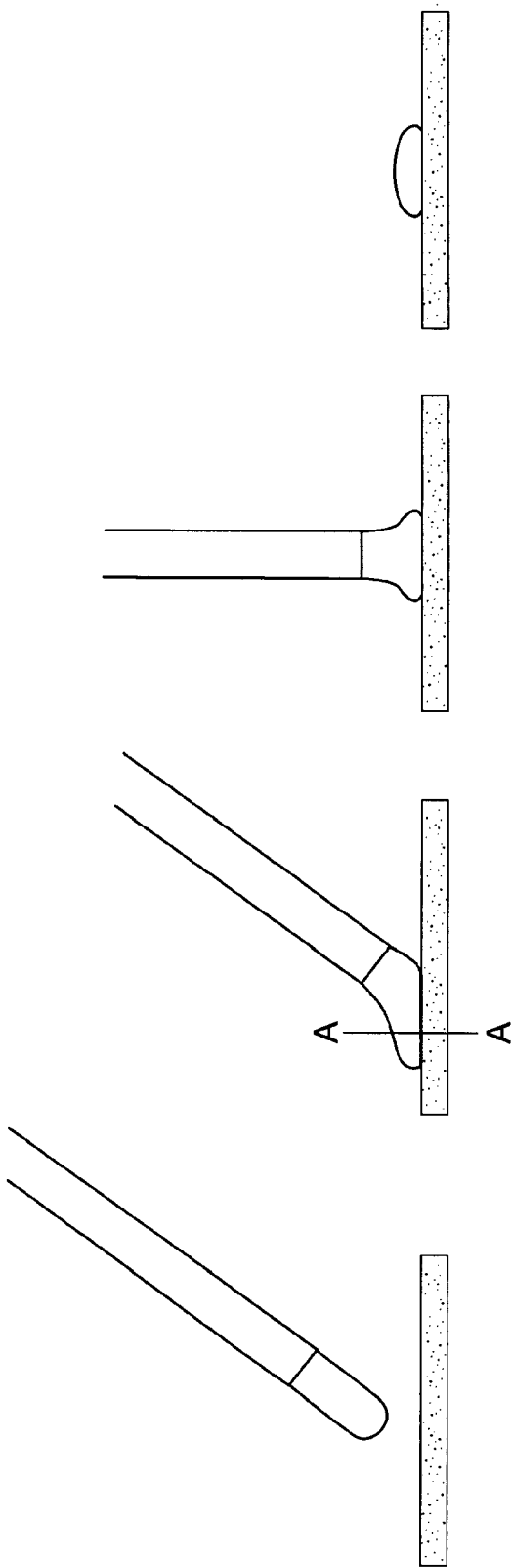

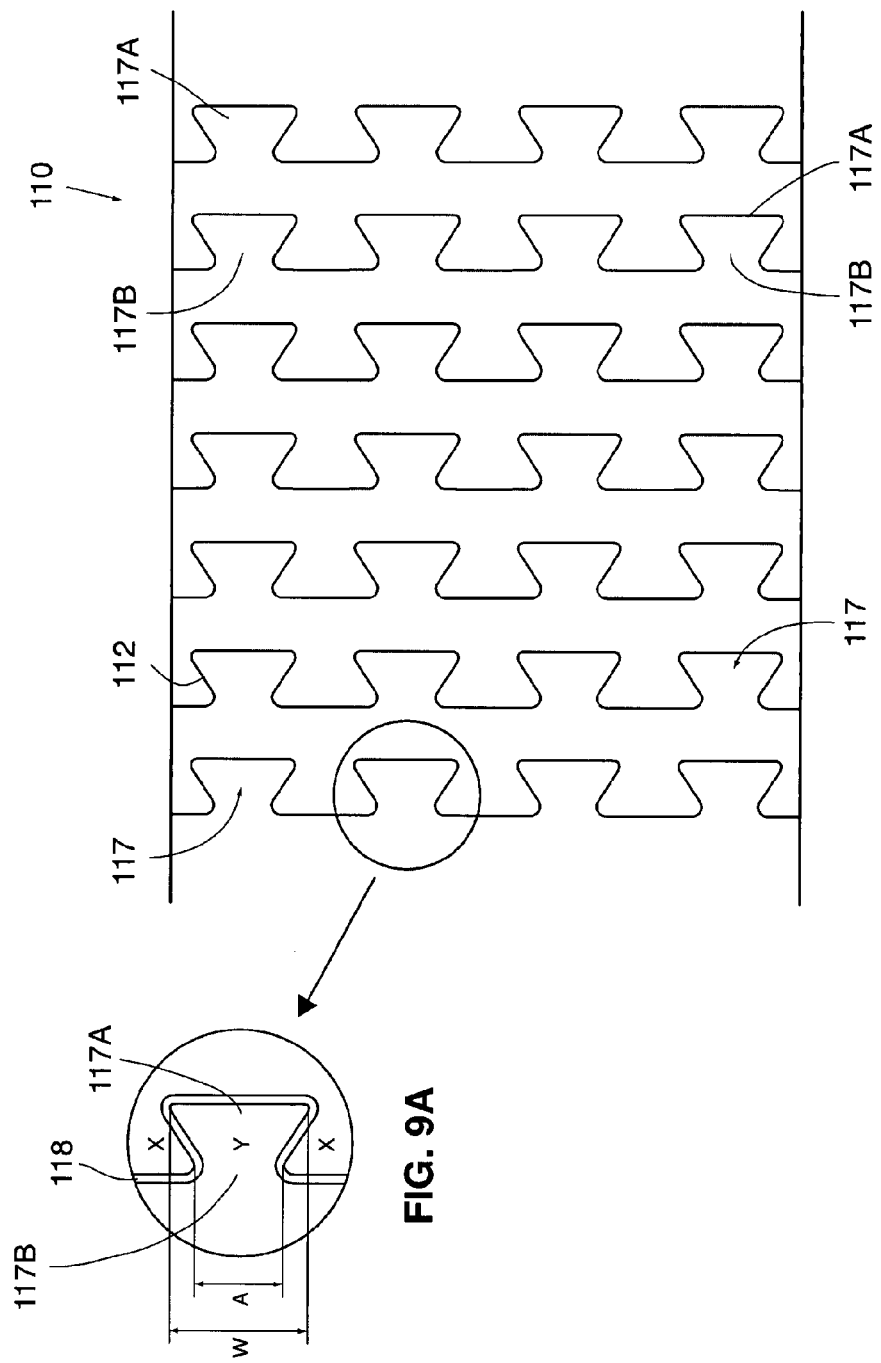

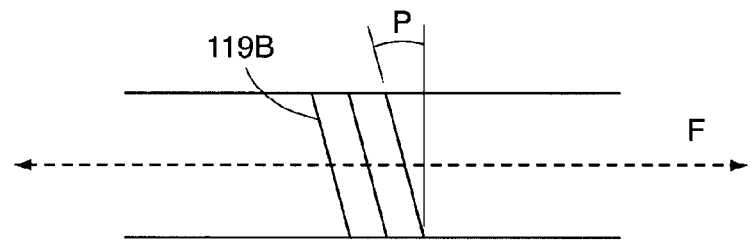
FIG. 12A
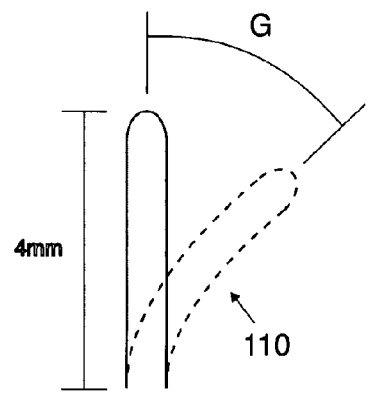
FIG. 12B
FIG. 12C     FIG. 12D

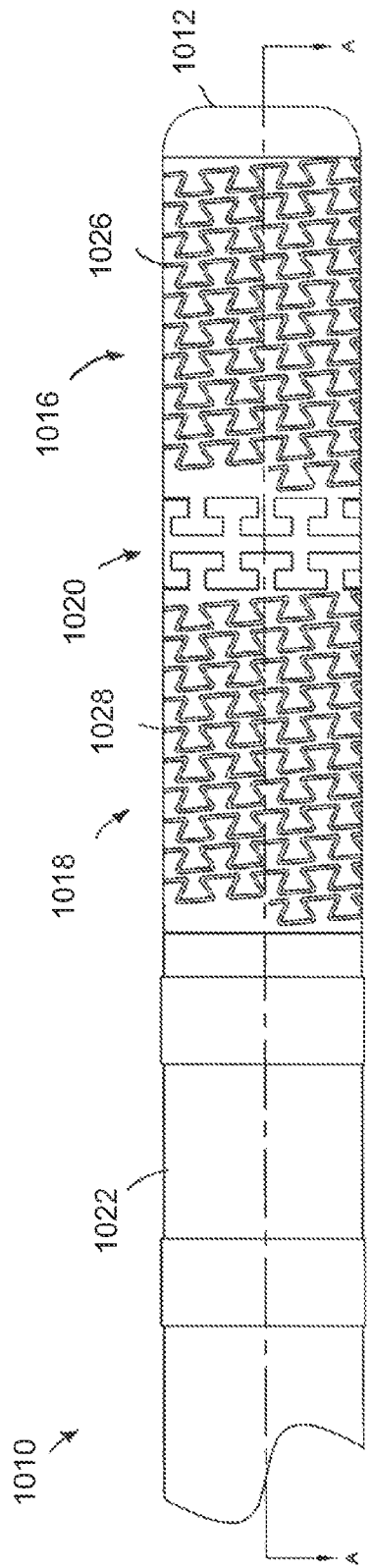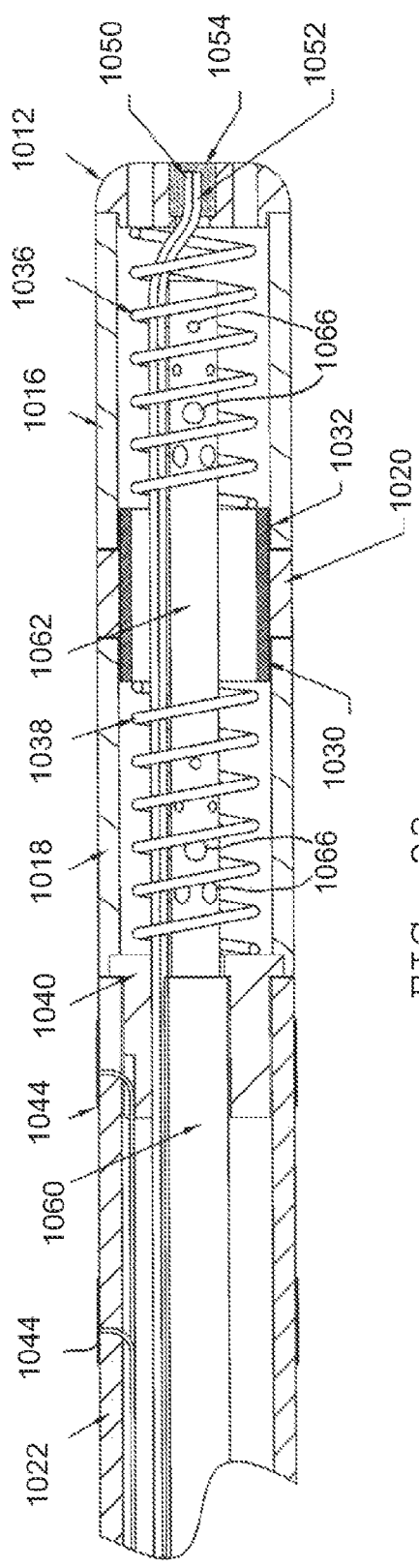

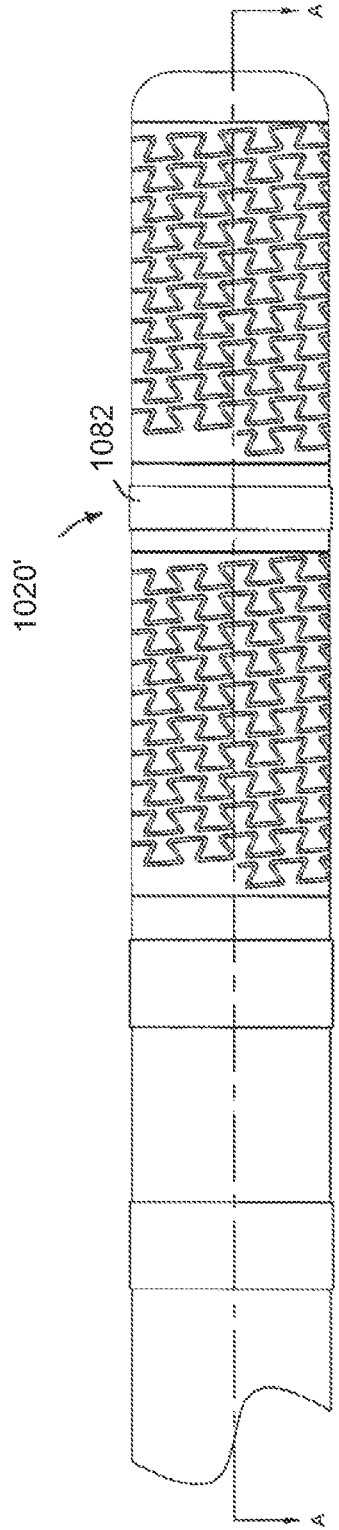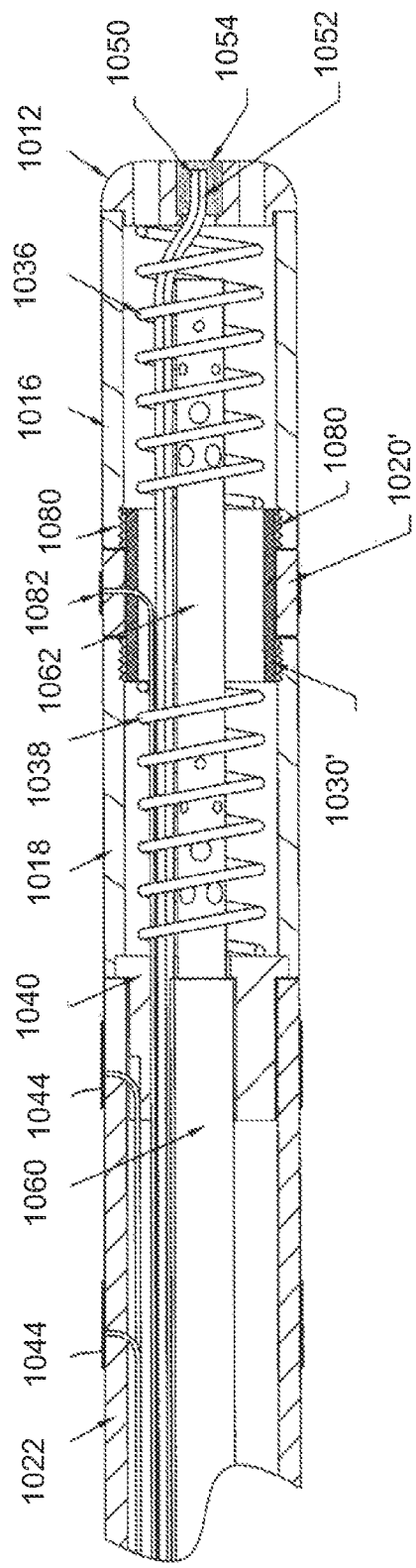

KIT FOR NON-INVASIVE ELECTROPHYSIOLOGY PROCEDURES AND METHOD OF ITS USE

CROSS-REFERENCE TO RELATED APPLICATIONS

This application is a continuation-in-part of U.S. application Ser. No. 12/651,074 filed 31 Dec. 2009 (the '074 application), and this application claims the benefit of U.S. provisional application No. 61/355,242 filed 16 Jun. 2010 (the '242 application). This application relates to U.S. patent application Ser. No. 11/853,759 filed 11 Sep. 2007 (the '759 application), which claims the benefit of U.S. provisional application No. 60/939,799, filed 6 Jun. 2007 (the '799 application). The '074, '242, '759 and '799 applications are hereby incorporated by reference as though fully set forth herein.

BACKGROUND OF THE INVENTION a. Field of the Invention

The instant invention relates to electrophysiology catheters. More specifically, the instant invention relates to flexible electrophysiology catheters that are particularly suitable for use with steerable introducer sheaths, including so-called pre-curved introducer sheaths that are manually manipulated to a desired target tissue location within the heart or vasculature (all of which are collectively to herein as steerable introducer sheaths).

b. Background Art

Catheters are used for an ever growing number of medical procedures. To name just a few examples, catheters are used for diagnostic, therapeutic, and ablative procedures. Typically, the physician manipulates the catheter through the patient's vasculature to the intended site, such as a site within the patient's heart. The catheter typically carries one or more electrodes (in the case of so-called "electrophysiology catheters") or other diagnostic or therapeutic devices, which may be used for ablation, diagnosis, cardiac mapping, or the like.

It is known that, to facilitate placement of the diagnostic or therapeutic catheter at a location of interest within the patient, it may be introduced through another catheter, commonly known as a "guiding catheter" or "introducer catheter," and the terms will be used interchangeably herein. Generally speaking, an introducer catheter is a tube having a high degree of directional control that is used to place other medical devices, including other catheters, which may have little or no directional control, into specific areas of the patient's body.

The path a catheter must navigate within a patient is often long and tortuous. It is known, therefore, to utilize one or more pull wires, which are typically offset from the central longitudinal axis of the catheter and which may be attached to one or more pull rings proximate the distal end of the catheter shaft, to manipulate the distal end of the catheter. For example, U.S. application Ser. No. 11/779,488, which is hereby incorporated by reference as though fully set forth herein, describes a steerable introducer catheter. Steerable electrophysiology catheters are also known.

BRIEF SUMMARY OF THE INVENTION

It has surprisingly been discovered that non-steerable electrophysiology catheters offer several advantages over prior art devices when used in conjunction with steerable introducers. For example, introducers provide enhanced precision and stability over steerable electrophysiology catheters. Similarly, because a non-steerable electrophysiology catheter need not be able to withstand the compressive forces to which a steerable catheter is subject, non-steerable electrophysiology catheters may be manufactured of softer polymers, thereby enhancing patient safety. Yet, the use of a steerable introducer allows the non-steerable electrophysiology catheter to be reliably navigated to a target site within the patient's vasculature. Certain tip electrode configurations described herein are also particularly desirable for use in connection with non-steerable electrophysiology catheters.

Disclosed herein is an electrophysiology catheter for use with a steerable introducer sheath. The electrophysiology catheter generally includes a flexible catheter body having a proximal end and a distal end and at least one hollow elongate tip electrode disposed at the distal end of the catheter body. The at least one hollow elongate tip electrode includes a sidewall having at least one elongate gap to provide flexibility in the sidewall for bending movement of the at least one hollow elongate tip electrode relative to a longitudinal axis of the catheter body, and the catheter body is an independent non-steerable structure. The flexible catheter body can also include an irrigation pathway extending from the proximal end to the distal end in order to permit an irrigation fluid to exit through the at least one elongate gap of the at least one hollow elongate tip electrode.

Also disclosed herein is a kit for performing non-invasive electrophysiology procedures. The kit generally includes a steerable introducer sheath having an interior lumen and an electrophysiology catheter. The electrophysiology catheter in turn includes: a flexible catheter body having a proximal end and a distal end; at least one hollow elongate tip electrode disposed at the distal end of the catheter body and including a sidewall having at least one elongate gap therein to provide flexibility in the sidewall for bending movement of the at least one hollow elongate tip electrode relative to a longitudinal axis of the catheter body; and a combination of a lumen having discrete lateral ports and a helical coil portion disposed within at least a portion of the at least one hollow elongate tip electrode, and wherein the catheter body comprises an independent non-steerable member. An outer diameter of the electrophysiology catheter is less than a diameter of the interior lumen of the steerable introducer, such that the electrophysiology catheter may be advanced through the steerable introducer sheath.

A method of ablating tissue is also disclosed herein. The method generally includes the steps of: directing a steerable introducer sheath having an interior lumen near target ablation tissue; placing, into the lumen of the steerable introducer sheath, a non-steerable electrophysiology catheter including a flexible catheter body having a proximal end, a distal end, at least one hollow elongate tip electrode disposed at the distal end of the catheter body, wherein the elongate tip electrode includes a sidewall having one or more elongate gaps to provide flexibility in the sidewall for bending movement of the at least one hollow elongate tip electrode relative to a longitudinal axis of the catheter body, and an interior structure configured to distribute irrigation fluid consistently within the at least one hollow elongate tip electrode, wherein said structure includes a helical coil and apertures formed in an lumen coupled to the helical coil; advancing the non-steerable electrophysiology catheter through the lumen of the steerable introducer sheath until the at least one hollow elongate tip electrode exits the distal tip of the steerable introducer sheath; directing the at least one hollow elongate tip electrode into contact with the target ablation tissue by steering the steerable introducer sheath; and activating the at least one hollow elongate tip electrode to apply energy to the target tissue so as to create a lesion.

The method can also include dragging the at least one hollow elongate activated tip electrode across the target tissue by steering the steerable introducer sheath.

Also disclosed herein is a method of mapping endocardial tissue including the steps of: generating a non-ionizing localization field around the endocardial tissue using a localization system; directing a steerable introducer sheath having an interior lumen to the endocardial tissue; placing a non-steerable electrophysiology catheter comprising a flexible catheter body having a proximal end and a distal end, and at least one hollow elongate tip electrode disposed at the distal end of the catheter body, the tip electrode comprising a sidewall having one or more elongate gaps to provide flexibility in the sidewall for bending movement of the at least one hollow elongate tip electrode relative to a longitudinal axis of the catheter body into the lumen of the steerable introducer sheath; advancing the non-steerable electrophysiology catheter through the lumen of the steerable introducer sheath until the tip electrode exits the distal tip of the steerable introducer sheath; moving the tip electrode around the endocardial tissue by steering the steerable introducer sheath and measuring a location of the tip electrode within the non-ionizing localization field; and aggregating multiple location measurements to create a map of the endocardial tissue.

In a first aspect of the disclosure, the sidewall of the at least one hollow elongate tip electrode is a substantially cylindrical sidewall.

In another aspect of the disclosure, the at least one elongate gap includes at least one annular gap extending around a portion of a circumference of the sidewall.

In still another aspect of the disclosure, the at least one elongate gap includes at least one helical gap that forms a helical pattern on the sidewall.

In a further aspect of the disclosure, the at least one elongate gap includes at least one zig-zag gap that forms a zig-zag pattern on the sidewall.

In yet another aspect of the disclosure, the at least one elongate gap includes at least one gap that defines alternating interlocking blocks.

In still another aspect of the disclosure, the at least one elongate gap includes at least one wavy gap that forms a wavy pattern on the sidewall.

Exemplary embodiments of the disclosure provide a flexible tip for an ablation catheter, the flexible tip having one, two, or more flexible electrode segments to produce multiple segmented ablation regions. In the case of two or more flexible electrode segments the adjacent flexible ablation electrode segments are electrically isolated from one another by an electrically nonconductive segment.

In accordance with an aspect of the present disclosure, a catheter apparatus comprises an elongate body having a distal end, a proximal end, and at least one fluid lumen extending longitudinally therein, with the fluid lumen comprising discrete ports and metallic coil extending therein; and a plurality of flexible electrode segments on a distal portion of the elongate body adjacent the distal end, each pair of neighboring flexible electrode segments being spaced from each other longitudinally by a corresponding electrically nonconductive segment. Each flexible electrode segment comprises a sidewall provided with one or more elongate gaps extending through the sidewall, the one or more elongate gaps providing flexibility in the sidewall for bending movement relative to a longitudinal axis of the catheter body.

In accordance with another aspect of the present disclosure, the electrically nonconductive segment spaced between each pair of neighboring flexible electrode segments can include a ring or other electrode spaced from the pair of flexible electrode segments. In this aspect the distance of the spacing of the electrode from each of the flexible electrode segments can vary between each flexible electrode segment and between embodiments.

In accordance with another aspect of the present disclosure, the neighboring flexible electrode segments can also be used as sensing electrodes.

Various additional objects, features, aspects, and advantages of the present invention will become more apparent from the following detailed description of the invention, along with the accompanying drawings in which like numerals represent like components.

BRIEF DESCRIPTION OF THE DRAWINGS

FIG. 2 is a perspective view of another embodiment of a flexible tip electrode that may be used in connection with a non-steerable electrophysiology catheter in accordance with the teachings herein.

FIGS. 2A-2D are alternative embodiments of the flexible tip electrode shown in FIG. 2.

FIGS. 7A-7C and 8A-8C illustrate the use of various flexible tip electrodes that may be used in connection with a non-steerable electrophysiology catheter in accordance with the teachings herein.

FIG. 8D is a cross-sectional view of line A-A in FIG. 8B.

FIG. 8E illustrates electrode-to-surface area in FIG. 8C.

FIG. 9 is a side view of an embodiment of a flexible tip electrode with an interlocking block pattern, such as may be used in connection with a non-steerable electrophysiology catheter in accordance with the teachings herein.

FIG. 9A is a close-up view of a block from the interlocking block pattern of FIG. 9.

FIG. 12A is an illustrative view of the degree of pitch of the spiraling member.

FIG. 12B is an illustrative view of the degree of flexing for the flexible tip electrode.

FIG. 12C is an illustrative view of an embodiment of the tip electrode being dragged across tissue with ridges.

FIG. 12D is an illustrative view of an embodiment of the tip electrode being dragged across smooth tissue surface.

FIG. 21 is an elevational view of a distal portion of an ablation catheter according to a first embodiment of the present disclosure.

FIG. 22 is a partial cross-sectional view of the distal portion of the ablation catheter of FIG. 21.

FIG. 23 is an elevational view of a distal portion of an ablation catheter according to a second embodiment of the present disclosure.

FIG. 24 is a partial cross-sectional view of the distal portion of the ablation catheter of FIG. 23.

DETAILED DESCRIPTION OF THE INVENTION

Figure 1A:
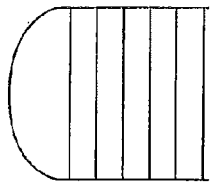
FIGS. 1A-1C are alternative embodiments of the flexible tip electrode shown in FIG. 1.

The invention and its various embodiments can now be better understood by turning to the following detailed description of the preferred embodiments, which are presented as illustrative examples of the invention defined in the claims. It is expressly understood that the invention as defined by the claims may be broader than the illustrated embodiments described below.

Many alterations and modifications may be made by those having ordinary skill in the art without departing from the spirit and scope of the invention. Therefore, it must be understood that the illustrated embodiments have been set forth only for the purposes of example and that they should not be taken as limiting the invention as defined by the following claims. For example, notwithstanding the fact that the elements of a claim are set forth below in a certain combination, it must be expressly understood that the invention includes other combinations of fewer, more, or different elements, which are disclosed herein even when not initially claimed or described in such combinations.

In one aspect, the present invention includes a non-steerable electrophysiology catheter having a flexible tip electrode usable, for example, to create linear lesions in tissue. As used herein, the term "non-steerable" means the catheter lacks independent directional control. That is, a non-steerable catheter, while sufficiently flexible to navigate through a patient's vasculature, cannot be separately controlled, as by the use of pull wires or other known steering mechanisms.

Though many different flexible tip electrode configurations are described herein, such flexible tip electrodes are generally hollow cylindrical structures including a lumen and having a round, dome-shaped terminal end. The wall of the flexible tip electrode may have many openings of various shapes, sizes, and overall configurations as described herein, all of which lend flexibility to the electrode.

The terms "spiral" and "spiraling," when used herein in conjunction with an electrode wall and its patterns, refer to circling configurations where a series of loops are formed on differing planes. The loops have substantially the same diameter, and resemble a coiled spring. These terms do not refer to circling on the same plane with increasing circumference.

The terms "gap" and "opening," when used herein in conjunction with a pattern cut in an electrode wall, refer to perforations that are more than a "groove," which is a surface cut that does not cut through the thickness of the wall. That is, the term "groove," as used herein, means a surface channel that does not perforate through the wall of the electrode; "gaps" and "openings," on the other hand, are perforated through the thickness of the electrode wall. Wherever a groove is mentioned in this application, however, it should be understood that the groove can optionally be replaced by a gap in alternative embodiments of the invention, and vice-versa.

A flexible tip electrode advantageously increases electrode-to-tissue surface area, which in turn improves lesion formation. Especially in tissue where ridges are present, the flexible tip electrodes disclosed herein can be dragged across such ridges with improved continuous electrode-to-tissue contact. Moreover, the flexible tip electrodes contemplated herein provide enhanced patient safety, as they reduce the likelihood of puncture when pressed against target tissue.

Flexible Tip Electrodes

Figure 1B:
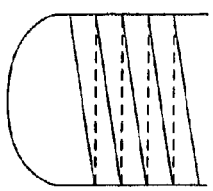
Figure 1:
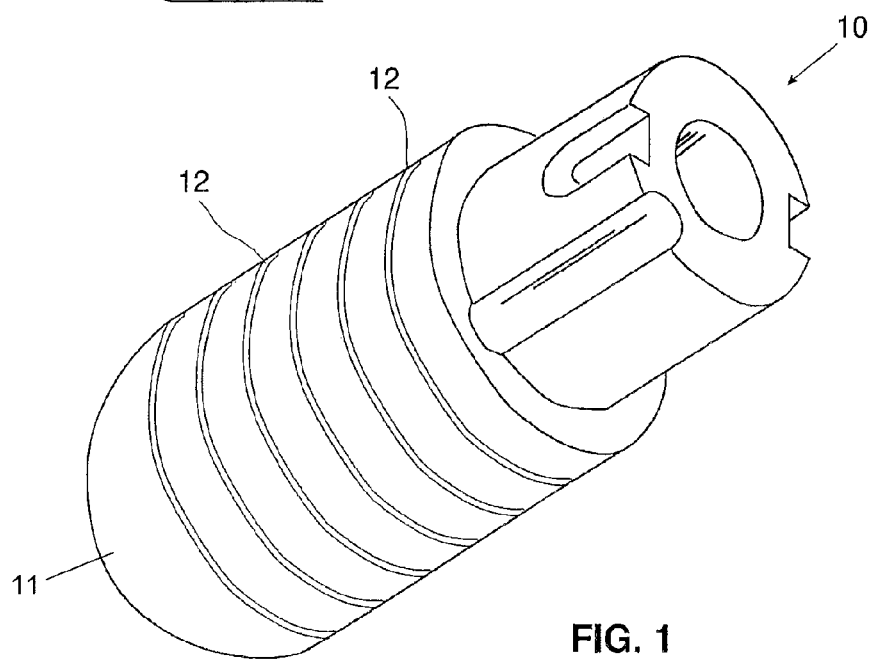
FIG. 1 is a perspective view of an embodiment of a flexible tip electrode that may be used in connection with a non-steerable electrophysiology catheter in accordance with the teachings herein.
Figure 1C:
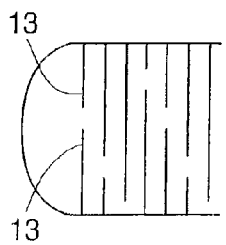

Referring now to FIG. 1, one flexible tip electrode 10 has a dome tip 11 and a series of ring-like grooves 12 disposed about the tip electrode, spaced substantially equidistant from each other along a longitudinal length of the tip electrode. Each ring-like groove 12 may form a continuous loop (as it is shown in FIG. 1A). Alternatively, all or part of the series of ring-like grooves can be in a spiral configuration (as shown in FIG. 1B) around the outside surface of the tip electrode. In another embodiment, the electrode may include some rings that do not form a continuous loop, but that rather have two terminal ends (13) spaced apart (as shown in FIG. 1C). Of course, alternative embodiments of flexible tip electrode 10 may include any combinations of these configurations.

As described above, the grooves illustrated in FIGS. 1, 1A, 1B, and 1C may be replaced by cutting patterns that are perforated through the thickness of the wall of the electrode (i.e., gaps or openings). Of course, if such a replacement is made in the embodiment shown in FIG. 1A, some type of additional supporting structure is required to connect the severed pieces together. For example, an inner coil may be provided within the lumen (see, for example, FIGS. 14A and 14B).

Referring now to FIG. 2, the grooves 12 are more spaced apart than those shown in FIG. 1. Here, each ring-like groove does not form a continuous loop, and terminal ends 13 of each groove slightly offset each other to maintain a desired degree of rigidity in the electrode. Note that in FIGS. 2A and 2B, the terminal ends 13 of the groove do not overlap. FIG. 2C illustrates another embodiment where the terminal ends 13 do overlap, although they do not meet to form a continuous loop. Another contemplated embodiment includes a combination of grooves with overlapping terminal ends and grooves with non-overlapping terminal ends. As is true with all embodiments disclosed in the instant application, grooves 12 may be replaced with cutting patterns that are perforated through the thickness of the electrode wall (i.e., gaps or openings).

FIG. 2D illustrates another embodiment where the ring-like grooves 12 are partial loops extending around a portion, such as about 180 degrees, of the electrode's cylindrical surface. Of course, many other positions of partial loops are also contemplated. That is, in certain embodiments of the invention, some or all of the grooves may extend around more or less than about 180 degrees of the electrode's cylindrical circumference.

Figure 3A:
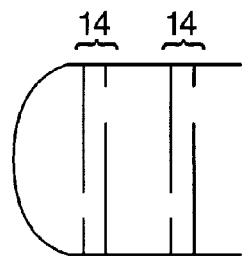
FIG. 3A is a side view of the embodiment shown in FIG. 3.
Figure 3:
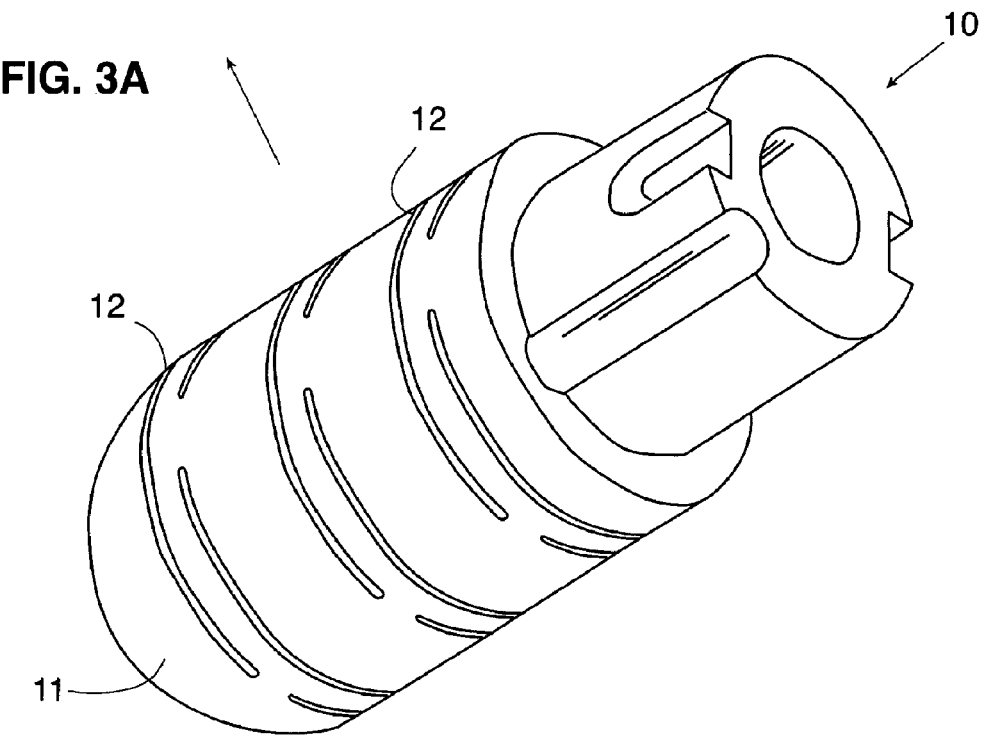
FIG. 3 is a perspective view of another embodiment of a flexible tip electrode that may be used in connection with a non-steerable electrophysiology catheter in accordance with the teachings herein.

In FIG. 3, three set of grooves 12 are provided, each set 14 (see FIG. 3A) having two non-continuous loops. As shown in FIG. 3A, the two grooves 12 in a single set 14 do not form a spiral. Spacing between the sets 14 is generally greater than the spacing between the grooves 12 in a single set, though, of course, this spacing can be adjusted without departing from the spirit and scope of the invention.

Figure 4A:
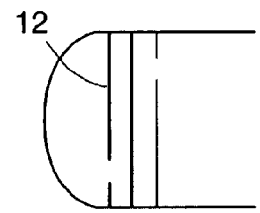
FIGS. 4A-4B are alternative embodiments of the flexible tip electrode shown in FIG. 4.
Figure 4B:
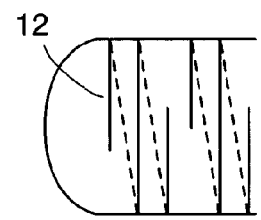
Figure 4:
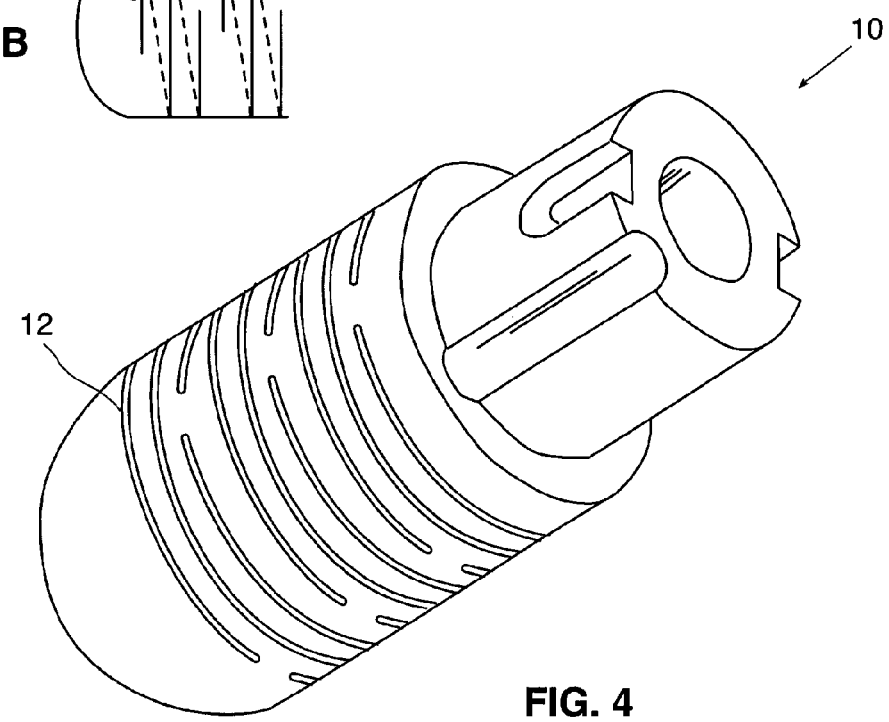
FIG. 4 is a perspective view of another embodiment of a flexible tip electrode that may be used in connection with a non-steerable electrophysiology catheter in accordance with the teachings herein.

Still another flexible electrode embodiment, illustrated in FIGS. 4, 4A, and 4B, provides sections of ring-like grooves 12. In the embodiment shown in FIG. 4A, the ring-like groove sections are non-continuous loops that do not connect with each other. In the embodiment shown in FIG. 4B, each section is a spiral groove 12 that is separate from each other section (i.e., the spiral grooves of adjacent sections do not connect).

Figure 5:
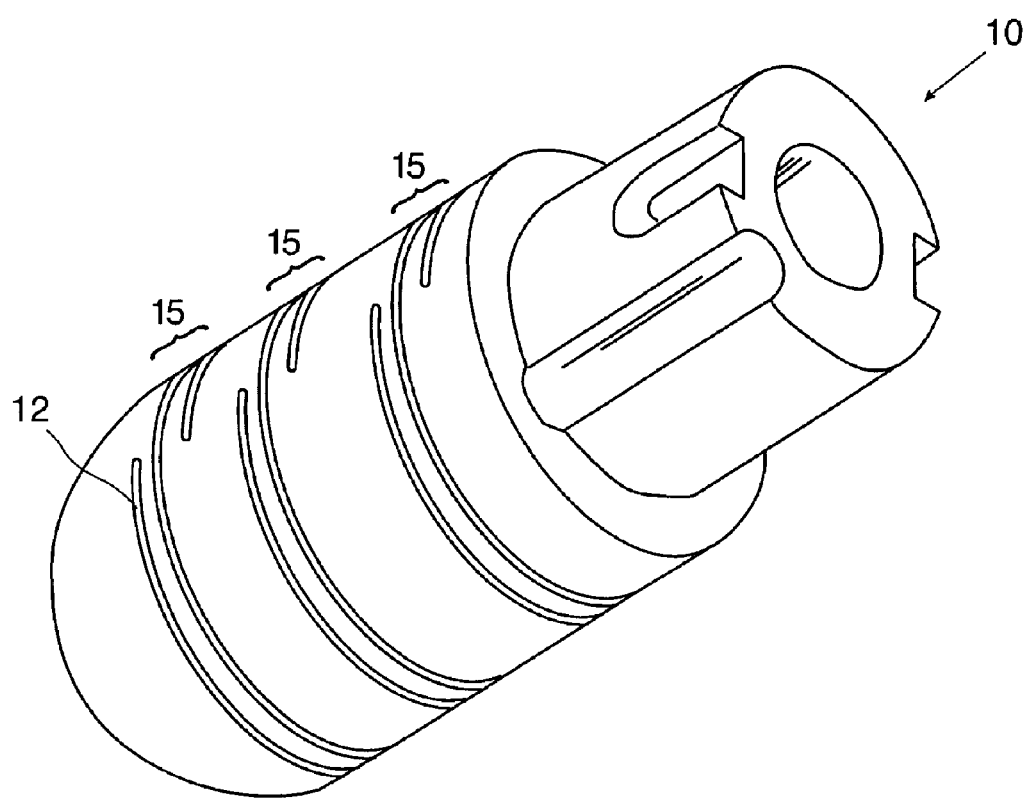
FIG. 5 is a perspective view of another embodiment of a flexible tip electrode that may be used in connection with a non-steerable electrophysiology catheter in accordance with the teachings herein.

FIG. 5 illustrates another embodiment of a flexible electrode 10 that includes three sets 15 of ring-like grooves 12. Each set 15 is shown to be a continuous spiral groove.

Figure 6:
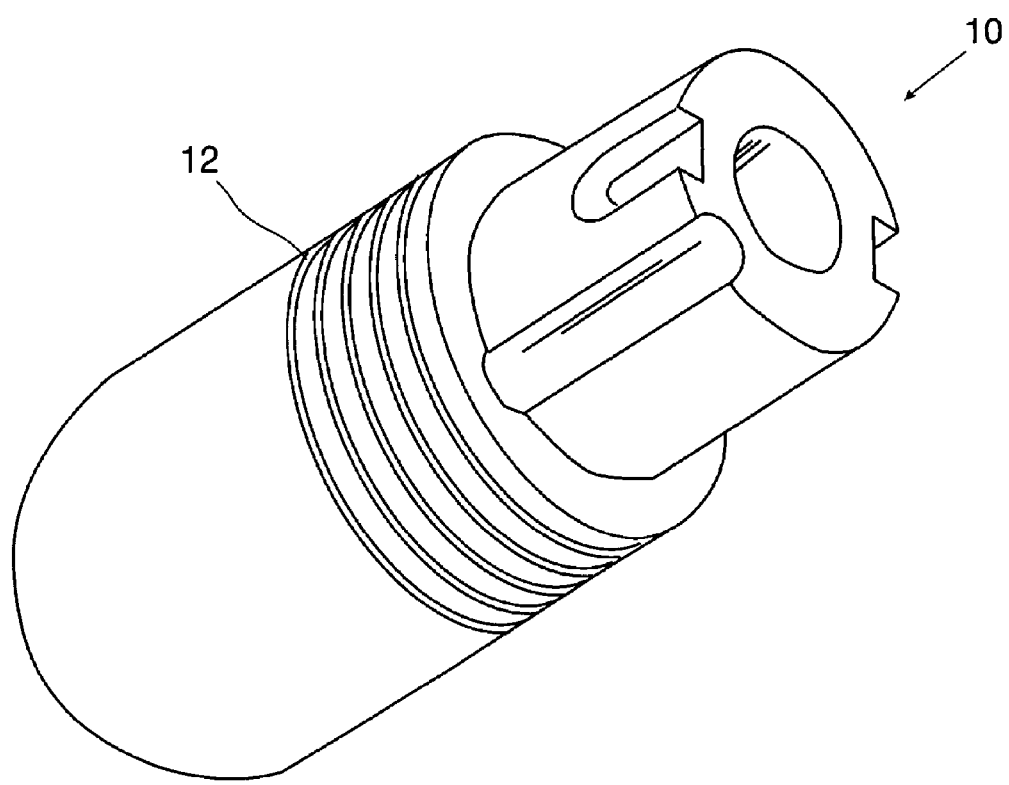
FIG. 6 is a perspective view of another embodiment of a flexible tip electrode that may be used in connection with a non-steerable electrophysiology catheter in accordance with the teachings herein.

FIG. 6 illustrates another contemplated embodiment of a flexible electrode 10 where a series of ring-like grooves 12 are disposed equidistant from each other along a proximal section of the tip electrode 10. Each ring-like groove 12 may or may not form a continuous loop. The embodiment depicted in FIG. 6 provides a degree of rigidity in the distal portion of the tip electrode 10.

FIGS. 7A through 7C illustrate a flexible electrode, such as described above, in operation. One advantageous aspect of the invention is that it facilitates dragging the flexible tip electrode 10 across a tissue surface. In such applications, the flexible electrode 10 deforms and/or flexes when it is dragged across a tissue surface, which desirably creates greater electrode-to-tissue surface area.

In FIG. 7A, the tip electrode 10 has a cut pattern 12 that includes relatively straight lines, which are perforated through the thickness of the electrode. FIG. 7B depicts a tip electrode 10 having a zig-zag design cutting pattern, which enhances the flexibility of tip electrode 10 above that of the configuration shown in FIG. 7A. FIG. 7C depicts a flexible tip electrode 10 having grooves 12 at the neck region (i.e., where the flexible tip electrode meets the catheter shaft), allowing for a degree of flexibility in a somewhat more rigid tip electrode.

FIGS. 8A through 8E illustrate how some embodiments of a flexible tip electrode may advantageously deform in other ways to create greater electrode-to-tissue surface area. In FIG. 8A, an embodiment of the electrode is ready to make contact with tissue surface. The electrode makes contact with the tissue surface (FIG. 8B) and the tip electrode deforms. A cross section area along line A-A becomes oval in shape (FIG. 8D). This embodiment not only flexes along a longitudinal axis, but also expands laterally. When the angle between the tissue surface and a longitudinal axis of the catheter body gets closer to a 90 degree angle (FIG. 8C), the flexible tip deforms and shortens due to downward pressure against the tissue surface. FIG. 8E shows a cross section of the tip electrode in FIG. 8C. The electrode-to-tissue surface area (represented by the circle in FIG. 8E) further expands outwardly (represented by arrows 16), as the catheter is pressed further towards the tissue surface. One contemplated embodiment that has the capability as shown in FIGS. 8A through 8E is the tip electrode with a zig-zag cut pattern as shown in FIG. 7B.

Referring now to FIG. 9, one preferred embodiment of flexible tip electrode 110 has a cut pattern that outlines alternating interlocking blocks 117. In this embodiment, the contemplated blocks 117 are disposed on both sides of the gap 118 (see FIG. 9A) created by the cutting pattern. Each block has a head 117A and a neck 117B, and the head is wider than the neck. In this interlocking pattern, a first head (represented by "Y" in FIG. 9A) of the block 117, which has a neck 117B connected to one side of the gap 118, is disposed between a second and third heads (represented by "X" and "Z" in FIG. 9A), both of which have necks 117B connected to the other side of the gap 118. These blocks 117 are interlocked because the wider head portion of one head is locked between the narrower neck portions of the two adjacent blocks 117. For example, the second and third heads ("X" and "Z") have a shortest distance A (shown as "A" in FIG. 9A) between the two heads, and distance A is shorter than a width (shown as "W" in FIG. 9A) of the first head.

Figure 10:
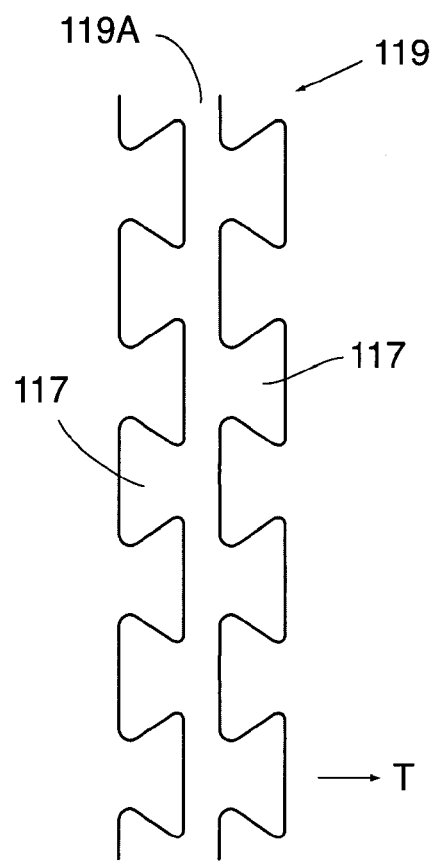
FIG. 10 is a view of a section of the electrode wall that makes up a stem with interlocking blocks.

Contemplated patterns of openings can also be described by focusing on the structures of the electrode wall, instead of focusing on the shape of the gap 118. For example, in FIG. 10, the contemplated electrode wall is comprised of a spiraling member 119. The member 119 spirals about a longitudinal axis of the electrode forming a series of loops (see FIG. 9), and the member 119 has both a stem 119A and a plurality of protruding blocks 117 disposed on both sides of the stem 119A. Each block 117 transversely extends (see arrow T in FIG. 10) toward an adjacent loop.

Figure 11:
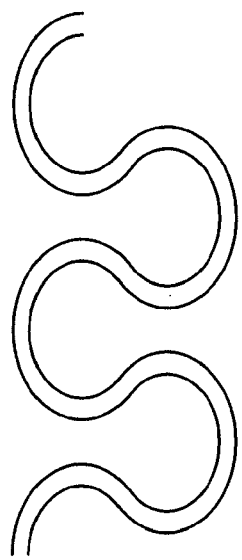
FIG. 11 is a view of an alternative design of bulbous interlocking blocks.

Contemplated blocks 117 can have various shapes. Typically, at least some of the blocks 117 are shaped like upside down triangles, where one angle of the triangle represents the neck region. Another desirable shape for blocks 117 is the bulbous shape shown in FIG. 11. Generally speaking, however, the heads of blocks 117 are wider than their necks.

Referring back to FIG. 9A, this embodiment includes a first head (Y) of a block 117 disposed between a second and third heads (X, Z) of two other blocks 117 that are connected to an adjacent loop. In another embodiment, a distance (A) between the second and third heads (X, Z) of an adjacent loop is shorter than a width (W) of the first head (Y), thereby restricting relative movement of two adjacent loops away from each other.

The member 119, having an axis 119B, spirals about the longitudinal axis with a pitch ("P" of FIG. 12A) between about 0.5 degrees and about 10 degrees inclusive. Put another way, the pattern of gaps 118 spirals around the longitudinal axis with a pitch between about 0.5 degrees and about 10 degrees inclusive.

In some embodiments of the invention, the patterns are of openings or gaps that are perforated through the entire thickness of the cylindrical wall to improve flexibility of the electrode. As used herein, the term "flexibility" refers to flexing and bending along the longitudinal length of the electrode. This flexibility allows an approximately 4 mm length of the electrode to bend in an angle G (see FIG. 12B) relative to the longitudinal axis that is preferably between about 0.2 degrees and about 70 degrees inclusive, more preferably between about 5 degrees and about 50 degrees inclusive, and most preferably about 45 degrees from a substantially straight position.

FIGS. 12C and 12D illustrate an electrode 110 being dragged across tissue 130. In FIG. 12C, the electrode 110 is flexed and pressed against tissue 130, which has an irregular (e.g., contoured or trabecular) surface. The flexibility of electrode 110 advantageously provides better contact with the target tissue, for example, in the trabeculated endocardial tissue where there are valleys, ridges, and pockets. As shown in FIG. 12C, electrode-to-tissue contact area is increased by using the side of the electrode 110 to deliver energy for ablation. The increased contact surface increases the likelihood of creating larger lesions at a given contact force and power setting. This enables deeper ablation without increased power, which is desirable because higher power settings undesirably increase the likelihood of coagulation.

In FIG. 12D, the dome tip 111 is used to deliver energy to tissue 130. Much like a suspension system in a vehicle, flexible electrode 110 absorbs any contraction or vibration of tissue 130, and proves continuous tissue contact in a beating heart during systole and diastole, substantially independent of the angle at which electrode 110 contacts the tissue 130, and regardless of whether electrode 110 is stationary or being dragged across tissue 130. Without such flexibility, a standard rigid tip electrode would "jump off" of the tissue in response to a beating heart.

Optionally, a flexible electrode may have force-sensing capability to measure contact force in different directions. For example, a strain gauge, a fiber optic sensor, or other sensors 140 may be disposed within the electrode to measure amount of force causing the electrode to flex, and to shorten. Such data can be collected and transmitted to the physician to monitor ablation progress. This may prevent accidental piercing of the target tissue when too much perpendicular force is applied to press the dome 111 into the tissue.

Unlike known elongate electrodes (e.g., U.S. Pat. No. 6,063,080), which can be laid across a tissue to create relatively longer linear lesions, the flexible electrodes disclosed herein have the unexpected advantage of improving precision in mapping and control at specific locations within the heart for more precise ablation, especially in relatively tight anatomical structures. Known elongate electrodes have difficulty positioning in such tight anatomical structures.

Another unexpected advantage offered by the flexible tip electrodes disclosed herein is minimized "flipping." When a standard rigid tip electrode is manipulated within a cavity having valleys and pockets, the tip electrode can get caught in the pocket when the physician continues to apply force in an attempt to move the tip electrode. In such instance, a standard rigid tip electrode would remain caught in the pocket until sufficient force is built, and the tip electrode suddenly "flip" out of the pocket. Such "flipping" is highly undesirable and should be avoided. The flexible tip electrodes disclosed herein greatly minimize "flipping," and allow smoother dragging across the valleys and pockets of irregular tissue surfaces.

Figure 13:
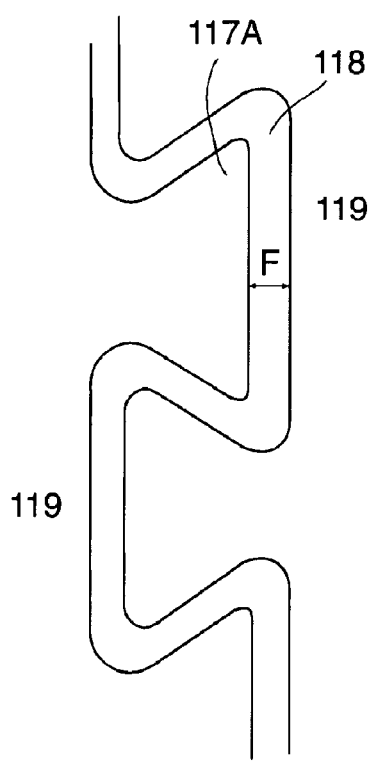
FIG. 13 is a close-up view of one embodiment of the gap in the electrode wall.

Refer now to FIG. 13, the openings in the wall provide a sufficient gap 118 in the wall to allow shortening of a length of the electrode, when a force is applied to the electrode in the linear (that is, axial) direction. The gap 118 disposed between a head 117A and a stem 119 of the adjacent loop, allows a freedom of movement ("F") between two adjacent loops relative to each other. Likewise, the gap 118 between adjacent heads 117A provides a freedom of movement for lengthening of the electrode along the longitudinal length of the electrode.

Preferably, the electrode can shorten between about 0.2% and about 10% inclusive of a resting length of the electrode. More preferably, the gap in the wall allows shortening of the electrode between about 0.1% and about 8% inclusive of the resting length of the electrode. Even more preferably, the gap in the wall allows shortening of the electrode between about 0.5% and about 5% inclusive of the resting length of the electrode. Still more preferably, the gap in the wall allows shortening of the electrode between about 0.1% and about 0.5% of the resting length of the electrode. This shortening advantageously and desirably reduces the likelihood of tissue piercing or puncture when the electrode is pressed into the tissue.

Figure 13A:
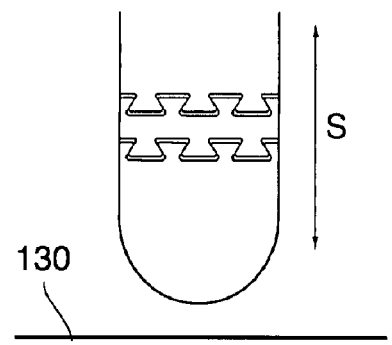
FIG. 13A is a side view of the electrode in FIG. 13 at rest.
Figure 13B:
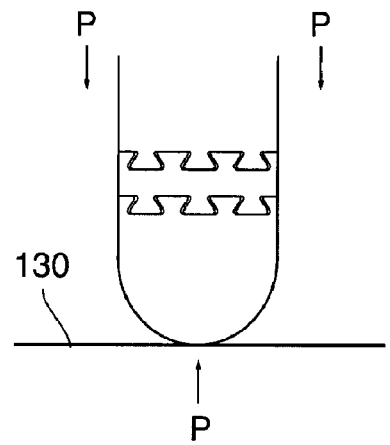
FIG. 13B is a side view of the electrode in FIG. 13 when pressed against a tissue surface.

In FIG. 13A, the electrode at rest has a freedom of movement ("F") shown, because the electrode at rest assumes a pre-determined shape stretching in the "S" direction. When the electrode is applied to a tissue 130, pressing force (arrows "P" in FIG. 13B) causes the electrode to shorten, against the stretching force "S." Once shortened, the width of the gap illustrating freedom of movement ("F") is minimized (see FIG. 13B).

Figure 14A:
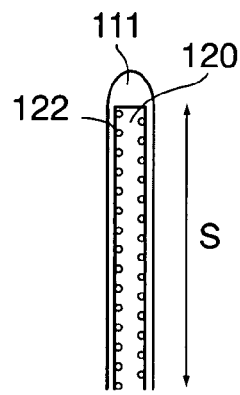
FIG. 14A is a longitudinal cross-sectional view of one embodiment of the tip electrode having a coil at rest.
Figure 14B:
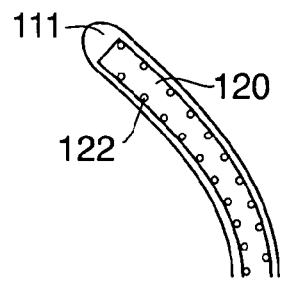
FIG. 14B is a longitudinal cross-sectional view of another embodiment of the tip electrode having a coil with an arcuate shape at rest.

The stretching force "S" may be provided by shape memory alloy in the electrode wall. Alternatively, FIG. 14A shows a cross sectional view of an electrode where the stretching force "S" is provided by a coil 122 in the lumen 120. The coil 122 provides structural integrity to the electrode and resiliently biases the electrode into a pre-determined configuration when resting. In one embodiment, the pre-determined configuration is straight. In another embodiment, the pre-determined configuration into which the electrode is biased is an arcuate shape (see FIG. 14B). The contemplated coil resiliently biases the electrode to stretch in an endwise direction ("S" in FIG. 14A) parallel to the longitudinal axis of the electrode. In other words, the coil optionally biases the tip electrode to stretch lengthwise.

The coil, the electrode, or both, can be formed of shape memory metal such as nitinol. The flexible tip electrode can be made of suitable conductive and biocompatible materials, suitable for ablation temperature; such materials include natural and synthetic polymers, various metals and metal alloys, nitinol, naturally occurring materials, textile fibers, and any suitable combinations thereof. For example, one embodiment of the tip electrode includes MP35N® alloy.

The flexible tip electrodes described above may be manufactured by providing a hollow cylindrical electrode and applying a laser or other cutting device to the cylindrical electrode in order to cut partially (thereby forming grooves) or entirely (thereby forming gaps or openings) through the electrode wall.

The cutting device cuts the wall in a pre-determined pattern. For example, as shown in FIG. 15, the cutting device may create a gap 118 that is consistently wider in some sections (M) and narrower in other sections (N). The wider sections (M) may be substantially parallel to a longitudinal axis of a spiral loop. The narrower sections (N) connect wider sections (M) together, and may be disposed generally transverse to the longitudinal axis of the spiral loop. The wider sections (M) allow freedom of movement between adjacent spiral loops, making it possible to shorten the electrode when a force is applied at a distal end of the electrode towards a proximal end.

Figure 15A:
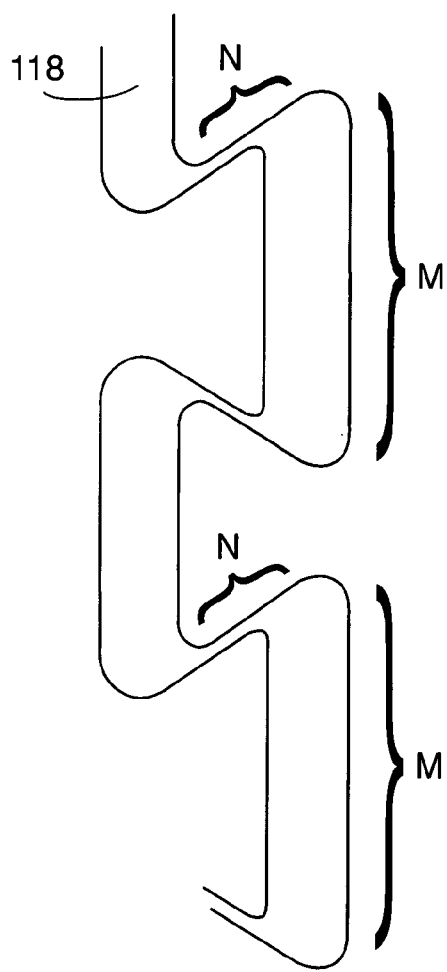
FIG. 15A is an illustrative view showing the shape and width of the gap as is cut by laser.
Figure 15B:
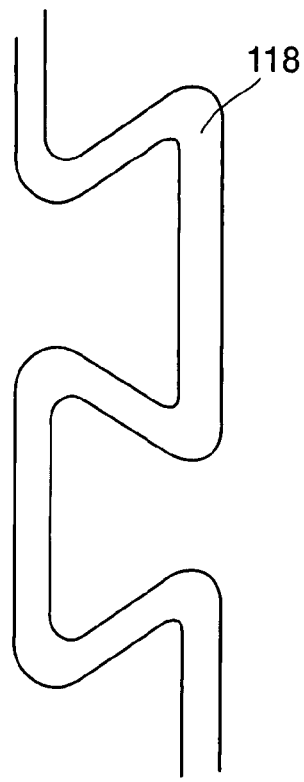
FIG. 15B is an illustrative view showing a consistent width of the gap as is cut by laser.
Figure 16:
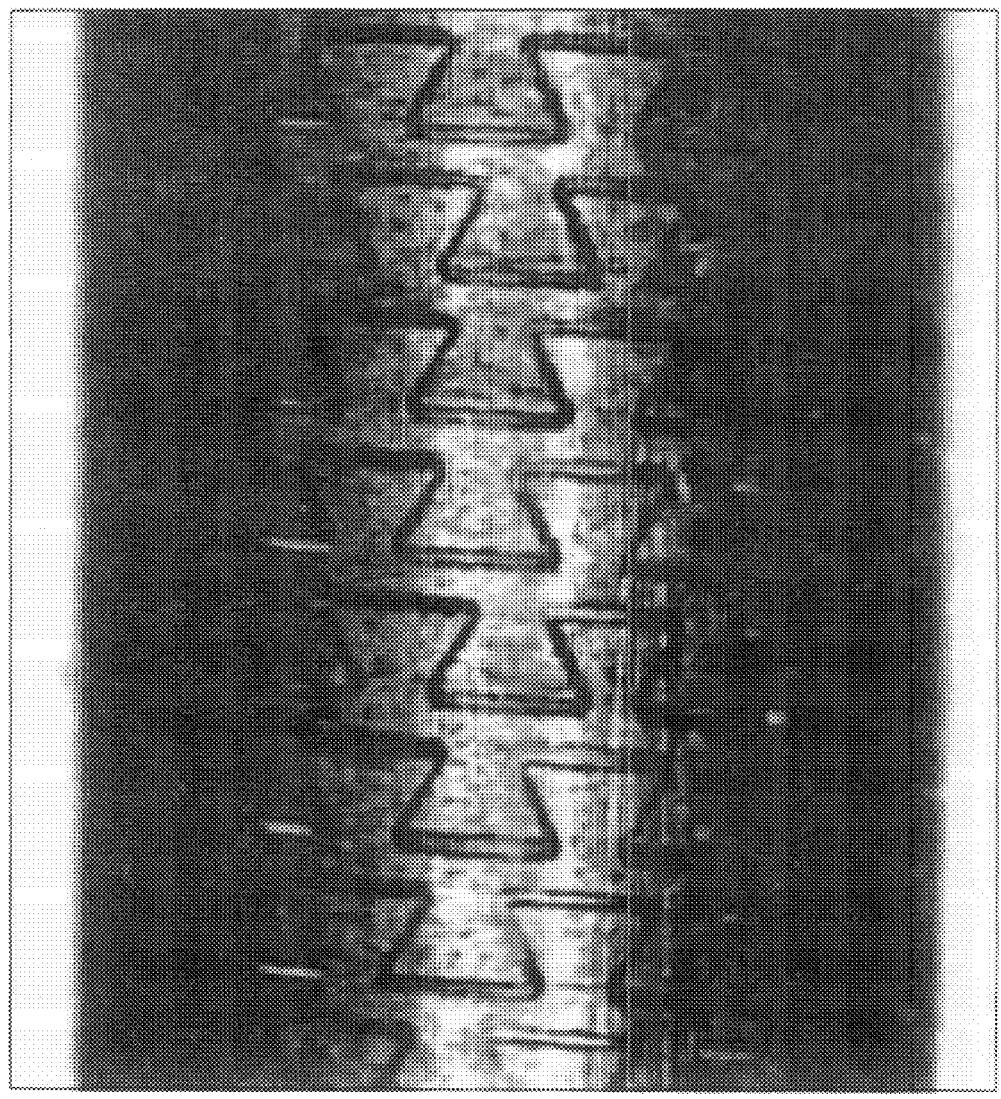
FIG. 16 is a photograph of an embodiment of the present invention, illustrating size and dimension of interlocking blocks in relative to the width of the catheter tip. The entire width of the catheter tip is shown.
Figure 17:
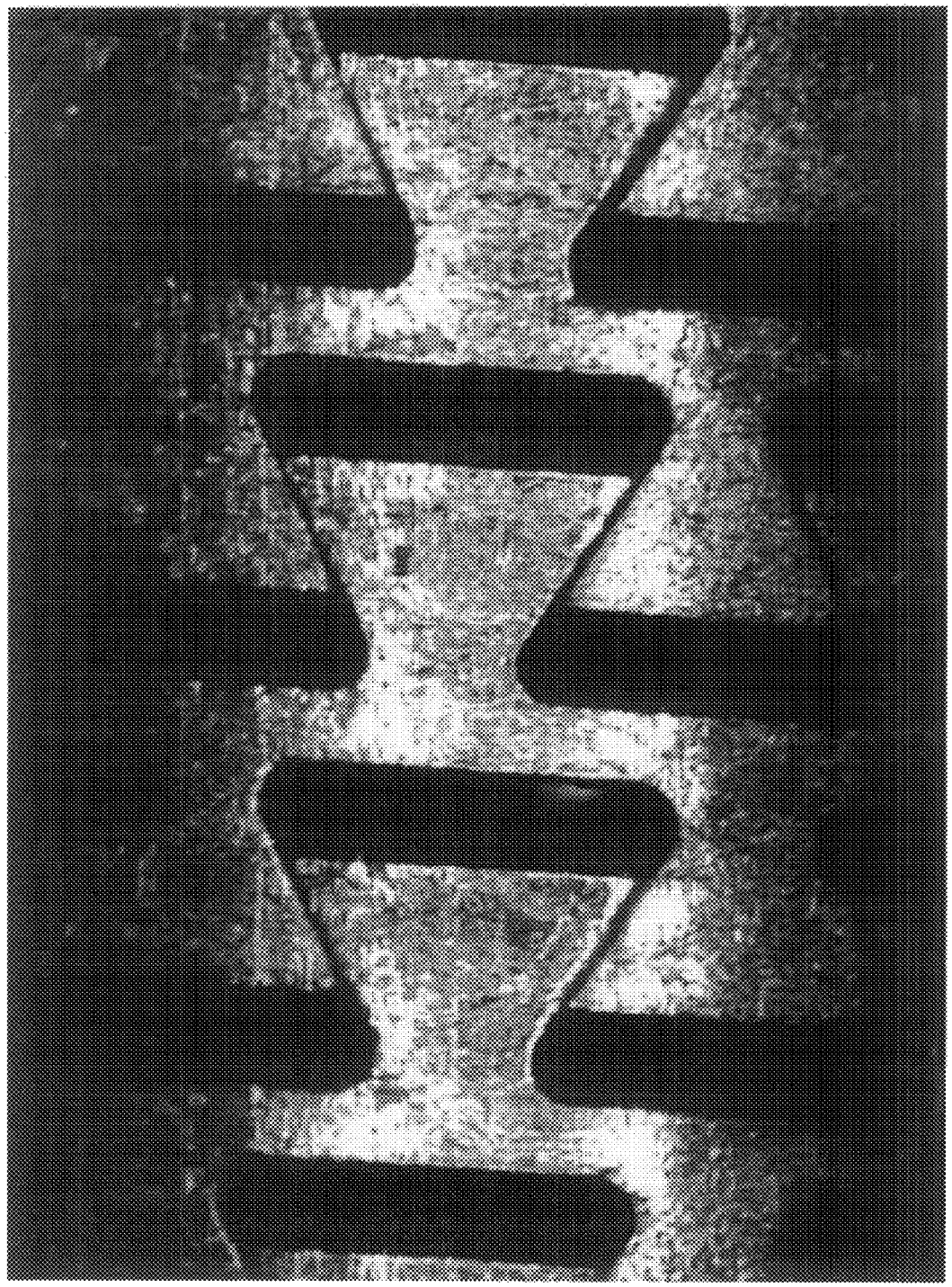
FIG. 17 is a close-up photograph of an embodiment of the interlocking blocks. The entire width of the catheter tip is not shown here.

FIG. 15B illustrates another embodiment where the cutting device cuts the wall in a pre-determined pattern where the gap 118 created by the laser has a generally constant width. A coil may subsequently be installed in the lumen of this electrode to provide stretching force to create wider sections and narrower sections as illustrated in FIG. 15A.

Coatings such as gold and platinum can also be applied to the electrode to increase thermo-conductivity. The electrode can also be coated with heparin to provide anticoagulation effect. In addition, the electrode may be electro-polished to reduce sharp edges.

One of ordinary skill in the art will appreciate that the flexible tip electrodes described above may be used to good advantage in both diagnostic and therapeutic procedures. For example, the flexible tip electrodes disclosed herein may be used to form linear ablation lesions in order to treat various cardiac rhythm disorders. Alternatively or additionally, the flexible tip electrodes disclosed herein may be used to perform electrophysiological ("EP") mapping.

Electrophysiology Catheters Having Flexible Tip Electrodes

As one of ordinary skill in the art will readily appreciate, the flexible tip electrodes described above may be connected in any suitable fashion to the distal end of a catheter shaft to form an electrophysiology catheter. Optionally, such an electrophysiology catheter may be an irrigated electrophysiology catheter, i.e., coupled to an irrigation system that delivers a fluid through a lumen in the catheter and that allows the fluid to pass outside of the flexible tip electrode, such as through the gaps or openings formed therein. Of course, an electrophysiology catheter can also be coupled to an energy source, such as a radio frequency (RF) generator to provide energy needed for tissue ablation, and/or to a diagnostic system, such as a system for mapping cardiac electrical activity. These optional aspects of the present invention will be familiar to those of ordinary skill in the art, and thus need not be described in detail herein.

As discussed above, the various flexible tip electrodes described herein may be used to good advantage in connection with non-steerable electrophysiology catheters. Such non-steerable electrophysiology catheters offer surprising benefits, including enhanced patient safety, when used cooperatively with steerable introducer catheters.

Typical steerable catheters must be made of harder polymers that can withstand the compressive forces applied to the catheter shaft length by the steering mechanisms used therein. Because the electrophysiology catheters of the present invention are designed to be used with a steerable introducer sheath, however, they need not include an independent steering mechanism. Thus, softer polymers, which minimize the risk of trauma to tissue, may be used to form the body of a non-steerable electrophysiology catheter according to the present invention. These softer polymers also desirably allow for greater catheter flexibility.

Electrophysiology catheter construction and manufacture will be generally familiar to those of ordinary skill in the art. Thus, the construction of a non-steerable electrophysiology catheter will not be described in detail herein except as necessary to understand the details of the present invention. By way of example only, and in order to aid those of ordinary skill in the art in understanding the instant disclosure, U.S. patent Ser. No. 11/967,220, filed 30 Dec. 2007, which is hereby incorporated by reference as though fully set forth herein, discloses one suitable catheter shaft and method of manufacturing the same.

Figure 18:
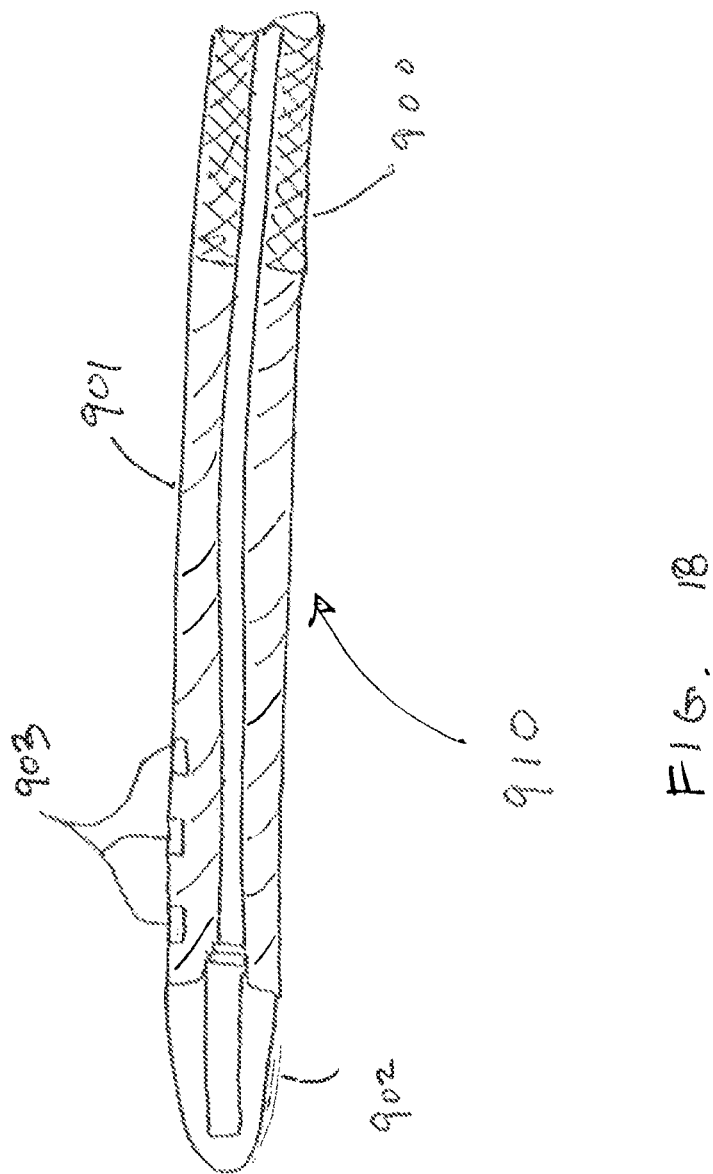
FIG. 18 is a view of an illustrative non-steerable electrophysiology that may be used in accordance with the teachings herein.

FIG. 18 depicts a portion of a non-steerable electrophysiology catheter 910. The proximal shaft 900 of catheter 910 can be made from one or more extruded melt processing polymers, such a polyether block amide (e.g., PEBAX™) or polytetrafluoroethylene (e.g., TEFLON. One of ordinary skill in the art will readily appreciate, of course, that any similar thermoplastic elastomer suitable for use in medical devices may be used to form proximal shaft 900. Likewise, the distal shaft 901 of catheter 910 can also be made from any thermoplastic elastomer suitable for use in medical devices. Preferably, the polymer used to from distal shaft 901 is softer than that used to form proximal shaft 900. Proximal shaft 900 and/or distal shaft 901 may also include a reinforcing or torque transfer layer, such as a braid layer, as generally known in the art.

FIG. 18 also illustrates the optional inclusion of three spot electrodes 903 disposed on distal shaft 901 near the distal end. Of course, more or fewer spot electrodes could be employed without departing from the scope of the invention. Likewise, ring electrodes (not shown) may be used instead of, or in addition to, spot electrodes 903. Spot electrodes 903 may be used as secondary ablation electrodes, as mapping electrodes, and/or to localize (that is, determine the position and/or orientation of) catheter 910 in a non-ionizing localization field (for example, as described in U.S. application Ser. No. 12/347,271, filed Dec. 31, 2008, which is hereby incorporated by reference as though fully set forth herein). Moreover, spot electrodes 903 could be replaced by magnetic localization elements when non-steerable electrophysiology catheter 910 is intended for use with a magnetic-field based localization system.

Flexible tip electrode 902, which may be any of the embodiments described above, is attached to the distal end of distal shaft 901.

Steerable Introducers

Catheter 910 is flexible, but does not contain any independent means of steering or deflecting the catheter 910. That is, catheter 910 will generally conform to the shape of a lumen that it is placed in, but the surgeon operating the catheter 910 will not be able to independently move or direct the catheter 910 into a specific orientation on its own.

Accordingly, to navigate the non-steerable electrophysiology catheters contemplated herein through a patient's vasculature, the use of a steerable introducer sheath, such as the Agilis™ Steerable Introducer of St. Jude Medical, Atrial Fibrillation Division, is desirable. The use and manufacture of steerable introducer sheaths are generally known in the art, and thus will not be described in detail herein except as necessary to understand the present invention. By way of example only, and to aid those of ordinary skill in the art in understanding the instant disclosure, U.S. application Ser. No. 11/779,488, filed 18 Jul. 2007, which is hereby incorporated by reference as though fully set forth herein, discloses one suitable steerable introducer and its method of manufacture. Likewise, U.S. Pat. No. 7,691,095, which is also incorporated by reference as though fully set forth herein, describes a control handle for a steerable introducer.

Figure 19:
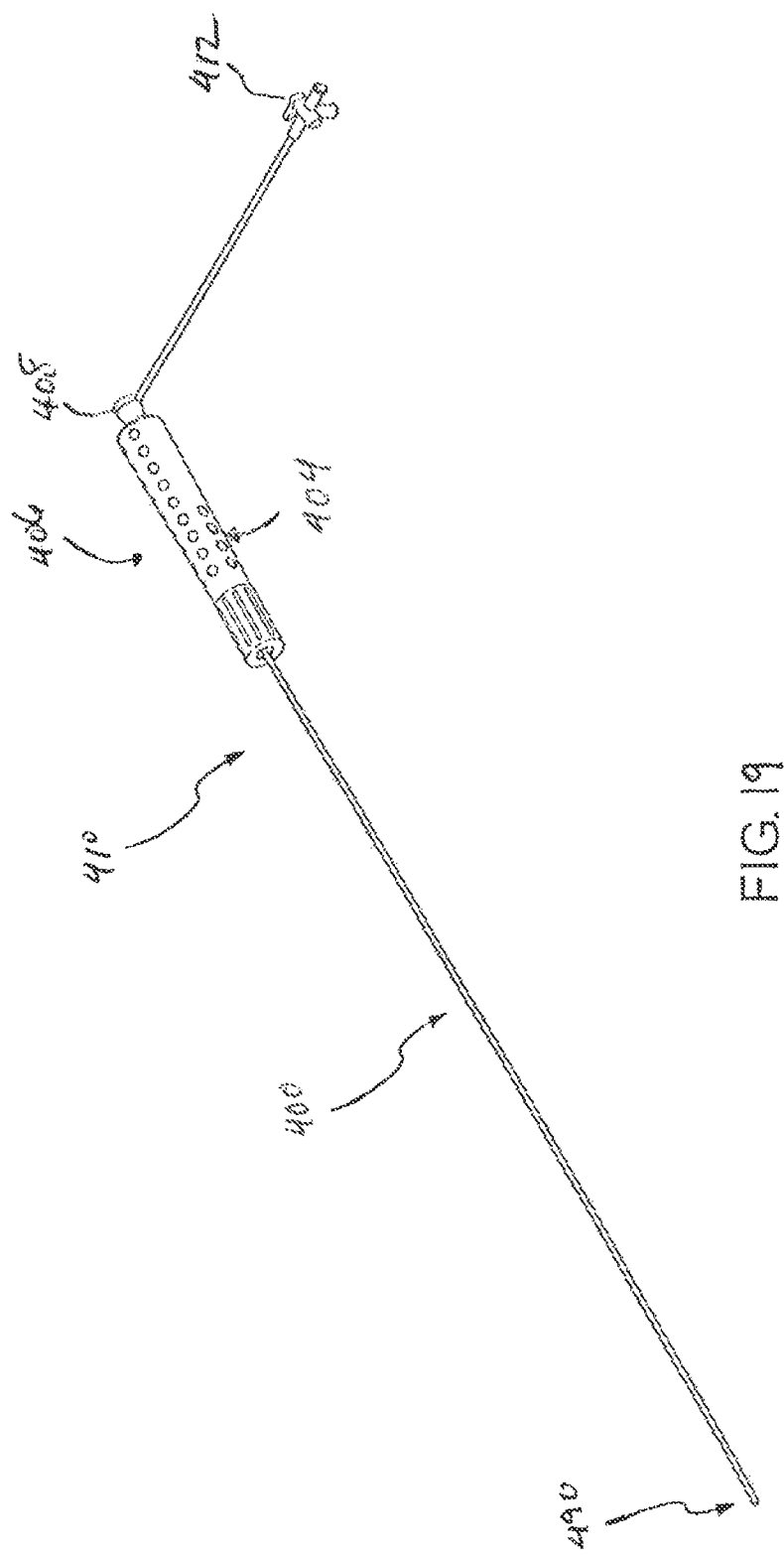
FIG. 19 is a perspective view of an illustrative steerable introducer that may be used in accordance with the teachings herein.

FIG. 19 is a perspective view of a steerable introducer assembly 410 such as may be used in accordance with the teachings herein. Introducer assembly 410 includes an introducer 400 having a distal end 490 and a proximal end 404. The introducer 400 may be operably connected to a handle assembly 406 which assists in guiding or steering the introducer during procedures. The introducer assembly 410 may optionally further include a hub 408 operably connected to an inner lumen (not shown) within the handle assembly 406 for insertion or delivery of catheter assemblies (such as non-steerable electrophysiology catheter 910 described above), fluids, or any other devices known to those of ordinary skill in the art. Optionally, the introducer assembly 400 further includes a valve 412 operably connected to the hub 408.

Use of the Present Invention

Figure 20C:
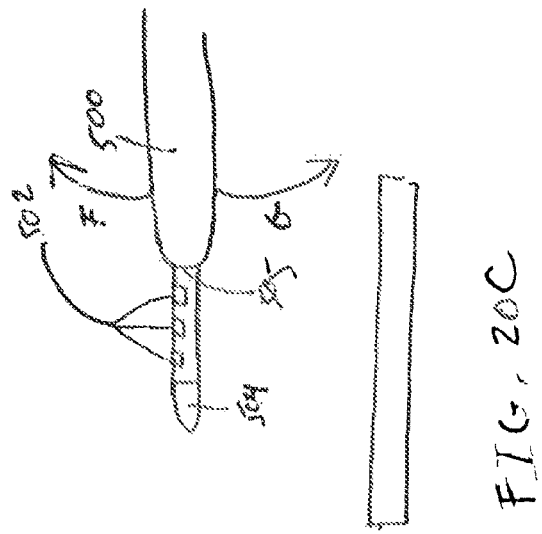
FIGS. 20A-20C are views of an embodiment of an ablation kit according to an aspect of the present invention in use.
Figure 20B:
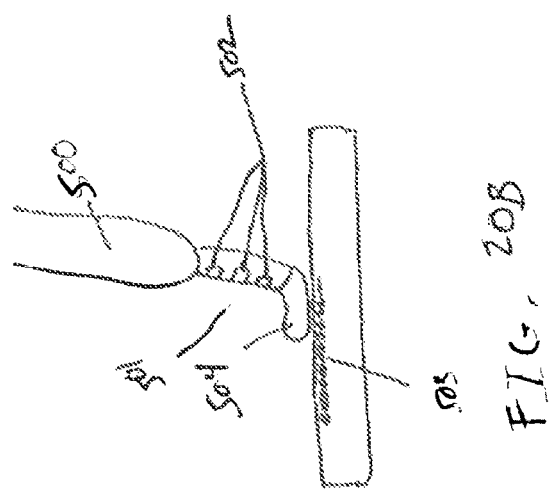
Figure 20A:
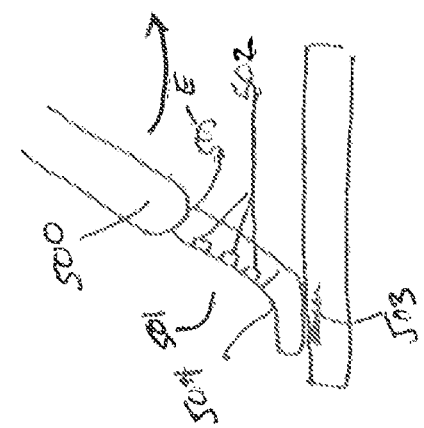

FIGS. 20A-20C depict the present invention in use. As shown in FIGS. 20A and 20B, steerable introducer sheath 500 is first navigated through the patient's vasculature, as known in the art, until its distal end is near the target tissue 503. A non-steerable electrophysiology catheter 501 is then inserted into steerable introducer sheath 500 via its proximal end (not shown in FIGS. 20A and 20B, but visible as 408 in FIG. 19). Non-steerable electrophysiology catheter 501 is then pushed through the steerable introducer sheath 500 until it exits steerable introducer sheath 500 at opening 505. Flexible tip electrode 504 may then be brought into contact with target tissue 503.

Energy may then be applied to the flexible tip electrode 504, such that flexible tip electrode 504 begins to ablate target tissue 503. By steering or deflecting the steerable introducer sheath 500 in a direction E, flexible tip electrode 504 is dragged across target tissue 503, thereby creating a substantially linear lesion (see FIG. 20B). Advantageously, because of the use of flexible tip electrode 504, this lesion is created with minimized risk of trauma (e.g., puncture) to target tissue 503.

FIG. 20C depicts a catheter according to the present invention in use as a mapping catheter. Steerable introducer sheath 500 is first navigated through the patient's vasculature until it is positioned inside a cardiac chamber. Next, non-steerable electrophysiology catheter is inserted into and pushed through steerable introducer sheath 500 until it exits via opening 505. A non-ionizing localization field may then be generated by a localization system (not shown) around the cardiac chamber. The non-ionizing localization field may be used to measure the location of spot electrodes 502 and/or flexible tip electrode 504 within the localization field. By steering the steerable introducer sheath 500 within the cardiac chamber (e.g., arrows F and G) and measuring the location of the spot electrodes 502 and flexible tip electrode 504 at any given point, a map of the cardiac chamber may be created using the measured locations. Advantageously, the use of flexible tip electrode 504 helps minimize the risk of tissue trauma (e.g., puncture) should tip electrode 504 come into contact with the cardiac wall, whether intentionally or inadvertently.

FIG. 21 is an elevational view of a distal portion 1010 of an ablation catheter according to an embodiment of the present disclosure. The distal portion 1010 includes a distal end 1012 which is flat with a rounded corner but can have other shapes such as the shape of a dome in alternative embodiments. The distal portion 1010 further includes two flexible electrode segments 1016, 1018 which are separated by an electrically nonconductive segment 1020. The distal flexible electrode segment 1016 is coupled with the distal end 1012 and the proximal flexible electrode segment 1018 is coupled with a catheter shaft 1022. The flexible electrode segments 1016, 1018 each have a cylindrical sidewall with a series of annular or ring-like surface channels, gaps, grooves, or through-thickness openings 1026, 1028, respectively, cut or otherwise formed into the sidewall. Elongate gaps define elongate areas of decreased wall thickness and decreased cross-sectional area of the sidewall, while elongate openings extend completely through the thickness of the sidewall. As used herein, an elongate gap or opening preferably has a length that is at least about 3 times the width of the gap or opening, more preferably at least about 5 times, and most preferably at least about 10 times. Various configurations and details of the elongate gaps and openings are provided in WO/2008/147599. In FIG. 21, the elongate openings 1026, 1028 each form an interlocking pattern that follows a continuous spiral path configuration from one end of the flexible electrode segment to the other end.

The electrically nonconductive segment 1020 electrically isolates the two flexible electrode segments 1016, 1018. It also serves to connect and secure the two flexible electrode segments. As seen in FIG. 21, the nonconductive segment 1020 has T-shaped protrusions that match the corresponding T-shaped voids or cavities on the edges of the two flexible electrode segments 1016, 1018 to form interlocking connections to secure the coupling between the electrode segments 1016, 1018. Of course, other configurations can be used to form the connections. The nonconductive segment 1020 is made of polyimide or some other nonconductive material. It can be formed as a strip and then bent into a tubular shape to form the interconnecting coupling between the two electrode segments 1016, 1018. The length of the nonconductive segment 1020 is sufficiently small to allow the ablation zones of the two adjacent electrode segments to overlap in order to form a continuous lesion. This also preserves the overall flexibility of the distal portion 1010 of the ablation catheter by limiting the size of the nonconductive segment 1020, which is non-flexible or at least not as flexible as the flexible electrode segments 1016, 1018. The distal portion 1010 preferably has substantially continuous flexibility between the flexible electrode segments. In one example, the flexible electrode segments 1016, 1018 are each about 4 mm in length while the nonconductive segment 1020 is about 1 mm in length. Typically, the nonconductive segment 1020 is substantially smaller in length than the flexible electrode segments 1016, 1018 (e.g., preferably less than a half, more preferably less than a third, and most preferably less than a fourth).

FIG. 22 is a partial cross-sectional view of the distal portion 1010 of the ablation catheter of FIG. 21. A tube 1030 is disposed internally between the flexible electrode segments 1016, 1018, and is attached to the flexible electrode segments 1016, 1018 by an adhesive 1032 or the like. The tube 1030 can be a PEEK tube or it can be made of other suitable nonconductive materials. A distal spring coil 1036 is supported between the distal end 1012 and the tube 1030. A proximal spring coil 1038 is supported between the tube 1030 and a tip stem 40 which is disposed between and attached to the proximal electrode segment 1018 and the catheter shaft 1022. The spring coils 1036, 1038 provide resilient biasing supports for the flexible electrode segments 1016, 1018, respectively, particularly when the segments have through-thickness openings instead of grooves. The spring coils 1036, 1038 provide structural integrity to the electrode walls and resiliently maintain the flexible electrode segments 1016, 1018 in a pre-determined configuration in a resting state where no applied force is placed on the electrode. In the embodiment shown, the pre-determined electrode configuration at rest orients the longitudinal axis of each electrode segment to follow a straight line. In a different embodiment, the pre-determined configuration at rest can orient the longitudinal axes of the electrode segments along a curved or arcuate path (see, e.g., WO/2008/147599). The illustrated embodiments show one example of a straight path and another example of an arcuate path turning 22° for each flexible electrode segment for a total of 44° for two flexible electrode segments. The contemplated coils 1036, 1038 resiliently bias the electrode segments 1016, 1018 to axially stretch in the direction that is generally parallel to the longitudinal axes of the electrode segments 1016, 1018. In other words, the coils optionally bias the flexible electrode segments to stretch lengthwise. When deflected from the predetermined configuration under applied force, the electrode segments can resiliently return to the predetermined configuration when the applied force is released. The electrode segments 1016, 1018 are made of suitable conductive and biocompatible materials, suitable for ablation temperature; such materials include natural and synthetic polymers, various metals and metal alloys, nitinol, MP3SN alloy, naturally occurring materials, textile fibers, and combinations thereof. The coils 1036, 1038, or the electrode segments 1016, 1018, or both coils and electrode segments, can be fabricated from a shape memory material such as nitinol.

As seen in FIGS. 21 and 22, a pair of band electrodes 44 are provided on the catheter shaft 1022 and can be used for diagnostic purposes or the like. Conductor wires 1050 and thermocouples 1052 are provided. FIG. 22 shows urethane adhesive 1054 at the distal end 1012 for the conductor wire(s) 1050 and thermocouple(s) 1052; the conductor wires 1050 and thermocouples 1052 can also be provided at other locations at or near other electrodes or electrode segments.

FIG. 22 shows a lumen tubing 1060 leading distally to an extension lumen tubing 1062 which extends along much of the lengths of the two flexible electrode segments 1016, 1018. The extension lumen tubing 1062 defines an extended fluid lumen extending therethrough, and enables channeling fluid from the lumen tubing 1060 along a longitudinal length of the distal portion 1010. As such, the extended fluid lumen of the tubing 1062 is in fluid communication with the fluid lumen of the lumen tubing 1060, and the extension lumen tubing 1062 has openings 1066 of sizes and arrangements to provide a desired (e.g., substantially uniform) irrigation pattern or fluid flow within the distal portion 1010 flowing out of the elongate openings 1026, 1028 of the flexible electrode segments 1016, 1018. Additional details of an extension lumen tubing can be found in the '074 application.

FIG. 23 is an elevational view of a distal portion of an ablation catheter according to a second embodiment of the present disclosure. FIG. 24 is a partial cross-sectional view of the distal portion of the ablation catheter of FIG. 23. The second embodiment differs from the first embodiment in the configurations of the electrically nonconductive segment 1020' and tube 1030' and the connection they provide to the flexible electrode segments in the second embodiment instead of the electrically nonconductive segment 1020 and the tube 1030 in the first embodiment. In the second embodiment, the tube 1030' has external threads to engage inner threads of the electrically nonconductive segment 1020' and the two flexible electrode segments 1016, 1018, so as to provide threaded connection 1080. Another band electrode 1082 can be provided on the nonconductive segment 1020'.

FIGS. 21-24 show two flexible electrode segments. In other embodiments, there can be three or more flexible electrode segments. Each pair of neighboring flexible electrode segments are separated by an electrically nonconductive segment.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrophysiology catheter for use with a steerable introducer sheath comprising:
    a flexible catheter body having a proximal end and a distal end;
    at least two hollow elongate tip electrodes disposed at the distal end of the catheter body, the first and second hollow elongate tip electrodes each comprising a sidewall having at least one elongate gap to provide flexibility in the sidewall for bending movement of the at least two hollow elongate tip electrodes relative to a longitudinal axis of the catheter body, wherein each of the hollow elongate tip electrodes comprises an inner lumen that includes discrete lateral ports; and
    an electrically nonconductive segment separating the first and second hollow elongate tip electrodes,
    wherein the catheter body comprises an independent non-steerable structure.

2. The electrophysiology catheter according to claim 1, wherein each sidewall of the at least two hollow elongate tip electrodes is a substantially cylindrical sidewall.

3. The electrophysiology catheter according to claim 1, wherein the at least one elongate gap comprises at least one annular gap extending around a portion of a circumference of the sidewall.

4. The electrophysiology catheter according to claim 1, wherein the at least one elongate gap comprises at least one helical gap that forms a helical pattern on the sidewall.

5. The electrophysiology catheter according to claim 1, wherein the at least one elongate gap comprises at least one zig-zag gap that forms a zig-zag pattern on the sidewall.

6. The electrophysiology catheter according to claim 1, wherein the at least one elongate gap comprises at least one gap that defines alternating interlocking blocks.

7. The electrophysiology catheter according to claim 1, wherein the at least one elongate gap comprises at least one wavy gap that forms a wavy pattern on the sidewall.

8. The electrophysiology catheter according to claim 1, wherein the flexible catheter body comprises an irrigation pathway extending from the proximal end to the distal end and configured to permit an irrigation fluid to exit through the at least one elongate gap of the at least two hollow elongate tip electrodes.

9. A kit for performing non-invasive electrophysiology procedures comprising:
    a steerable introducer sheath having an interior lumen; and
    an electrophysiology catheter comprising
        a flexible catheter body having a proximal end and a distal end;
        at least one hollow elongate tip electrode disposed at the distal end of the catheter body, the at least one hollow elongate tip electrode comprising a sidewall having at least one elongate gap therein to provide flexibility in the sidewall for bending movement of the at least one hollow elongate tip electrode relative to a longitudinal axis of the catheter body; and
        a combination of a lumen having discrete lateral ports and a helical coil portion disposed within at least a portion of the at least one hollow elongate tip electrode, and wherein the catheter body comprises an independent non-steerable member; and
    wherein an outer diameter of the electrophysiology catheter is less than a diameter of the interior lumen of the steerable introducer, such that the electrophysiology catheter may be advanced through the steerable introducer sheath.

10. The kit as recited in claim 9, wherein the sidewall of the at least one hollow elongate tip electrode is a substantially cylindrical sidewall.

11. The kit as recited in claim 9, wherein the at least one elongate gap comprises at least one annular gap that extends around a portion of a circumference of the sidewall.

12. The kit as recited in claim 9, wherein the at least one elongate gap comprises at least one a helical gap that forms a helical pattern on the sidewall.

13. The kit as recited in claim 9, wherein the at least one elongate gap comprises at least one zig-zag gap that forms a zig-zag pattern on the sidewall.

14. The kit as recited in claim 9, wherein the at least one elongate gap defines alternating interlocking blocks.

15. The kit as recited in claim 9, wherein the at least one elongate gap comprises at least one wavy gap that forms a wavy pattern on the sidewall.

16. The kit as recited in claim 9, wherein the electrophysiology catheter further comprises an irrigation pathway extending from the proximal end of the catheter body to the distal end of the catheter body and configured to permit an irrigation fluid to exit through the at least one elongate gap of the at least one hollow elongate tip electrode.

17. A method of ablating tissue comprising:
directing a steerable introducer sheath having an interior lumen near target ablation tissue,
placing, into the lumen of the steerable introducer sheath, a non-steerable electrophysiology catheter comprising
a flexible catheter body having a proximal end and a distal end, and
at least two hollow elongate tip electrodes disposed at the distal end of the catheter body, the at least two hollow elongate tip electrode each comprising
a sidewall having one or more elongate gaps to provide flexibility in the sidewall for bending movement of the at least two hollow elongate tip electrodes relative to a longitudinal axis of the catheter body,
an electrically nonconductive segment separating the first and second hollow elongate tip electrodes; and
an interior structure configured to distribute irrigation fluid consistently within the at least two hollow elongate tip electrodes, wherein said interior structure includes a helical coil and discrete lateral ports formed in a lumen coupled to the helical coil,
advancing the non-steerable electrophysiology catheter through the lumen of the steerable introducer sheath until the at least two hollow elongate tip electrodes exit the distal tip of the steerable introducer sheath,
directing the at least two hollow elongate tip electrodes into contact with the target ablation tissue by steering the steerable introducer sheath,
activating the at least two hollow elongate tip electrodes to apply energy to the target tissue so as to create a lesion.

18. The method of claim 17, further comprising dragging the at least two hollow elongate activated tip electrodes across the target tissue by steering the steerable introducer sheath.

19. A method of mapping endocardial tissue comprising:
generating a non-ionizing localization field around the endocardial tissue using a localization system,
directing a steerable introducer sheath having an interior lumen to the endocardial tissue,
placing, into the lumen of the steerable introducer sheath, a non-steerable electrophysiology catheter comprising
a flexible catheter body having a proximal end and a distal end,
at least two hollow elongate tip electrodes disposed at the distal end of the catheter body, the at least two hollow elongate tip electrodes each comprising a sidewall having one or more elongate gaps to provide flexibility in the sidewall for bending movement of the at least two hollow elongate tip electrodes relative to a longitudinal axis of the catheter body, wherein each of the hollow elongate tip electrodes comprises an inner lumen that includes discrete lateral ports, and
an electrically nonconductive segment separating the first and second hollow elongate tip electrodes;
advancing the non-steerable electrophysiology catheter through the lumen of the steerable introducer sheath until the tip electrodes exit the distal tip of the steerable introducer sheath,
moving the tip electrodes around the endocardial tissue by steering the steerable introducer sheath and measuring a location of the tip electrodes within the non-ionizing localization field, and
aggregating multiple location measurements to create a map of the endocardial tissue.

20. A kit for performing non-invasive procedures, comprising:
a steerable introducer sheath having an interior lumen; and
a catheter configured to be inserted through the interior lumen of the steerable introducer sheath, the catheter comprising:
a flexible body having a proximal end and a distal end;
at least two hollow tip electrodes disposed at the distal end of the catheter body and each hollow tip electrode comprising a sidewall including an elongate gap therein, wherein the elongate gap renders the hollow tip electrodes flexible and bendable relative to a longitudinal axis of the body, wherein each of the hollow elongate tip electrodes comprises an inner lumen that includes discrete lateral ports, and
an electrically nonconductive segment separating the first and second hollow elongate tip electrodes;
wherein the catheter lacks structure to provide independent directional control thereto.

* * * * *